(12) United States Patent
Ameer et al.

(10) Patent No.: US 11,529,417 B2
(45) Date of Patent: Dec. 20, 2022

(54) WOUND HEALING THROUGH SIRT1 OVEREXPRESSION

(71) Applicant: Northwestern University, Evanston, IL (US)

(72) Inventors: Guillermo A. Ameer, Chicago, IL (US); Michele Jen, Dallas, TX (US); Jian Yang, Evanston, IL (US)

(73) Assignee: Northwestern University, Evanston, IL (US)

( * ) Notice: Subject to any disclaimer, the term of this patent is extended or adjusted under 35 U.S.C. 154(b) by 56 days.

(21) Appl. No.: 15/931,262

(22) Filed: May 13, 2020

(65) Prior Publication Data

US 2020/0384113 A1 Dec. 10, 2020

Related U.S. Application Data

(62) Division of application No. 15/529,288, filed as application No. PCT/US2015/062588 on Nov. 25, 2015, now Pat. No. 10,653,782.

(60) Provisional application No. 62/084,375, filed on Nov. 25, 2014.

(51) Int. Cl.
| | |
|---|---|
| *A01N 63/00* | (2020.01) |
| *A61K 47/32* | (2006.01) |
| *A61K 48/00* | (2006.01) |
| *A61K 9/00* | (2006.01) |
| *A61P 17/02* | (2006.01) |
| *A61K 38/50* | (2006.01) |
| *A61K 47/10* | (2017.01) |
| *A61K 47/34* | (2017.01) |
| *A61L 15/24* | (2006.01) |
| *A61L 15/44* | (2006.01) |
| *A61L 15/60* | (2006.01) |
| *A61L 15/62* | (2006.01) |
| *A61L 15/64* | (2006.01) |

(52) U.S. Cl.
CPC ............ *A61K 47/32* (2013.01); *A61K 9/0014* (2013.01); *A61K 38/50* (2013.01); *A61K 47/10* (2013.01); *A61K 47/34* (2013.01); *A61K 48/005* (2013.01); *A61K 48/0016* (2013.01); *A61L 15/24* (2013.01); *A61L 15/44* (2013.01); *A61L 15/60* (2013.01); *A61L 15/62* (2013.01); *A61L 15/64* (2013.01); *A61P 17/02* (2018.01); *C12Y 305/01* (2013.01); *A61L 2300/412* (2013.01); *A61L 2300/604* (2013.01); *A61L 2430/34* (2013.01); *C12N 2800/95* (2013.01)

(58) Field of Classification Search
None
See application file for complete search history.

(56) References Cited

U.S. PATENT DOCUMENTS

| | | | | |
|---|---|---|---|---|
| 7,776,326 | B2* | 8/2010 | Milbrandt | A61P 37/00 424/94.5 |
| 8,143,042 | B2 | 3/2012 | Bettinger et al. | |
| 8,758,796 | B2* | 6/2014 | Ameer | C12N 5/0692 424/423 |
| 9,211,363 | B2* | 12/2015 | Ameer | A61L 27/34 |
| 2005/0164969 | A1 | 7/2005 | Blander | |
| 2011/0113498 | A1 | 5/2011 | Westphal et al. | |
| 2014/0010861 | A1 | 1/2014 | Bancel et al. | |
| 2018/0303941 | A1 | 10/2018 | Ameer et al. | |
| 2018/0319810 | A1 | 11/2018 | Ellis et al. | |
| 2018/0338991 | A1 | 11/2018 | Sinclair et al. | |
| 2019/0048016 | A1 | 2/2019 | Ellis et al. | |

FOREIGN PATENT DOCUMENTS

| | | | |
|---|---|---|---|
| WO | WO 2002/031111 | * | 4/2002 |
| WO | WO 2002031111 | A2 | 4/2002 |
| WO | WO 2016086088 | A2 | 6/2016 |

OTHER PUBLICATIONS

Yang (Biomaterials, 2006, 27:1889-1898 (available online Nov. 15, 2005).*
Banks et al., SirT1 Gain of Function Increases Energy Efficiency and Prevents Diabetes in Mice, Cell Metab, vol. 8(4), pp. 333-341, 2008.
Bitar et al., Caveolin-1/PTRF upregulation constitutes a mechanism for mediating p53-induced cellular senescence: implications for evidence-based therapy of delayed wound healing in diabetes, Am J Physiol Endocrinol Metab, vol. 305(8), pp. E951-E963, 2013.
Blander et al., SIRT1 Promotes Differentiation of Normal Human Keratinocytes, J Invest Dermatol, vol. 129, pp. 41-49, 2009.
Branski et al., Gene therapy in wound healing: present status and future directions, GeneTher, vol. 14(1), pp. 1-10, 2007.
Brunet et al., Stress-dependent regulation of FOXO transcription factors by the SIRT1 deacetylase, Science, vol. 303(5666), pp. 2011-2015, 2004.
Clark, Oxidative Stress and "Senescent" Fibroblasts in Non-Healing Wounds as Potential Therapeutic Targets, J Invest Dermatol, vol. 128(10), pp. 2361-2364, 2008.
Dimri et al., A biomarker that identifies senescent human cells in culture and in aging skin in vivo, PNAS, vol. 92(20), pp. 9363-9367, 1995.

(Continued)

*Primary Examiner* — Michael C Wilson
(74) *Attorney, Agent, or Firm* — Casimir Jones SC; David W. Staple

(57) ABSTRACT

Compositions and methods are provided for improved wound healing. In particular, provided herein are compositions and methods for the direct delivery of Sirtuin-1 (Sirt1) or vectors encoding Sirt1 to the wounds (e.g., of diabetic patients).

4 Claims, 11 Drawing Sheets

Specification includes a Sequence Listing.

(56) References Cited

OTHER PUBLICATIONS

Eming et al., Inflammation in Wound Repair: Molecular and Cellular Mechanisms, J Invest Dermatol, vol. 127(3), pp. 514-525, 2007.
Fan et al., SIRT1 Regulates UV-lnduced DNA Repair through Deacetylating XPA, Mol Cell, vol. 39(2), pp. 247-258, 2010.
Fenton et al., Cellular Senescence After Single and Repeated Balloon Catheter Denudations of Rabbit Carotid Arteries, Arterioscler Thromb Vasc Biol, vol. 21, pp. 220-226, 2018.
Galiano et al., Quantitative and reproducible murine model of excisional wound healing, vol. 12(4), pp. 485-492, 2004.
Galiano et al., Topical Vascular Endothelial Growth Factor Accelerates Diabetic Wound Healing through Increased Angiogenesis and by Mobilizing and Recruiting Bone Marrow-Derived Cells, Am J Pathol, vol. 164(6), pp. 1935-1947, 2004.
Gillum et al., SirT1 Regulates Adipose Tissue Inflammation, Diabetes, vol. 60(12), pp. 3235-3245, 2011.
Gurard-Levin et al., Peptide Arrays Identify Isoform-Selective Substrates for Profiling Endogenous Lysine Deacetylase Activity, ACS Chem Biol vol. 5(9), pp. 863-873, 2010.
Hasegawa et al., Renal tubular Sirt1 attenuates diabetic albuminuria by epigenetically suppressing Claudin-1 overexpression in podocytes, Nat Med, vol. 19(11), pp. 1496-1504, 2013.
Herranz et al., Sirt1 improves healthy ageing and protects from metabolic syndrome-associated cancer syndrome, Nat Commun, vol. 1, article 3, 2010.
Kaeberlein et al., Substrate-specific activation of sirtuins by resveratrol, J Biol Chem, vol. 280(17), pp. 17038-17045, 2005.
Jen et al., Sustained, localized transgene expression mediated from lentivirus-loaded biodegradable polyester elastomers. J Biomed Mater Res Part A 2013:101A:1328-1335.
Kuo et al., Profiling Deacetylase Activities in Cell Lysates with Peptide Arrays and SAMDI Mass Spectrometry, Anal Chem, vol. 85(22), pp. 10635-10642, 2013.
Langley et al., Human SIR2 deacetylates p53 and antagonizes PML/p53-induced cellular senescence, EMBO J, vol. 21(10), pp. 2383-2396, 2002.
Lee et al., Overexpression of SIRT1 protects pancreatic βcells against cytokine toxicity through suppressing NF-κB signaling pathway, Diabetes, vol. 67(8), pp. 344-351, 2008.
Michishita et al., Evolutionarily Conserved and Nonconserved Cellular Localizations and Functions of Human SIRT Proteins, Mol Biol Cell, vol. 16(10), pp. 4623-4635, 2005.
Ming et al., Regulation of global genome nucleotide excision repair by SIRT1 through xeroderma pigmentosum C, PNAS, vol. 107(52), pp. 22623-22628, 2010.
Ming et al., Loss of sirtuin 1 (SIRT1) disrupts skin barrier integrity and sensitizes mice to epicutaneous allergen challenge. J Allergy Clin Immunol. Apr. 2015;135(4):936-45.
Orimo et al., Protective role of SIRT1 in diabetic vascular dysfunction, Arterioscler Thromb Vasc Biol, vol. 29(6), pp. 889-894, 2009.
Papanas et al., Benefit-Risk Assessment of Becaplermin in the Treatment of Diabetic Foot Ulcers, Drug Safety, vol. 33(6), pp. 455-461, 2010.
Potente et al., SIRT1 controls endothelial angiogenic functions during vascular growth, Genes Dev, vol. 21, pp. 2644-2658, 2007.
Qiang et al., Epidermal SIRT1 regulates inflammation, cell migration, and wound healing. Sci Rep. Oct. 26, 2017;7(1):14110.
Rodgers et al., Nutrient control of glucose homeostasis through a complex of PGC-1α and SIRT1, Nature, vol. 434, pp. 113-118, 2005.
Satoh et al., Sirt1 Extends Life Span and Delays Aging in Mice through the Regulation of Nk2 Homeobox 1 in the DMH and LH, Cell Metab, vol. 18(3), pp. 416-430, 2013.
Schafer et al., Oxidative stress in normal and impaired wound repair, Pharmacol Res, vol. 58(2), pp. 165-171, 2008.
Spallotta et al., A Nitric Oxide-dependent Cross-talk between Class I and III Histone Deacetylases Accelerates Skin Repair, J Biol Chem, vol. 288, pp. 11004-11012, 2013.
Su et al., Assays of Endogenous Caspase Activities: A Comparison of Mass Spectrometry and Fluorescence Formats, Anal Chem, vol. 78(14), pp. 4945-4951, 2006.
Sun et al., SIRT1 Improves Insulin Sensitivity under Insulin-Resistant Conditions by Repressing PTP1B, Cell Metab, vol. 6(4), pp. 307-319, 2007.
Takemura et al., Sirtuin 1 Retards Hyperphosphatemia-Induced Calcification of Vascular Smooth Muscle Cells, Arterioscler Thromb Vasc Biol, vol. 31, pp. 2054-2062, 2011.
Telgenhoff et al., Cellular senescence mechanisms in chronic wound healing, Cell Death Differ, vol. 12, pp. 695-698, 2005.
Toniolo et al., Regulation of SIRT1 in Vascular Smooth Muscle Cells from Streptozotocin-Diabetic Rats, PLoS One, vol. 8(5), pp. e65666, 2013.
Vasile et al., Differential expression of thymosin beta-10 by early passage and senescent vascular endothelium is modulated by VPF/VEGF: evidence for senescent endothelial cells in vivo at sites of atherosclerosis, FASEB J, vol. 15(2), pp. 458-466, 2001.
Vila et al., AAV8-mediated Sirt1 gene transfer to the liver prevents high carbohydrate diet-induced nonalcoholic fatty liver disease. Mol Ther Methods Clin Dev. Oct. 1, 2014;1:14039.
Warboys et al., Disturbed Flow Promotes Endothelial Senescence via a p53-Dependent Pathway, Arterioscler Thromb Vasc Biol, vol. 34, pp. 985-995, 2014.
Yang et al., Synthesis and evaluation of poly(diol citrate) biodegradable elastomers. Biomaterials. Mar. 2006;27(9):1889-98.
Yang et al., A Thermoresponsive Biodegradable Polymer with Intrinsic Antioxidant Properties, Biomacromolecules, vol. 15(11), pp. 3942-3952, 2014.
Yang et al., Macrophage α1-AMP-activated protein kinase (α1AMPK) antagonizes fatty acid-induced inflammation through SIRT1, J Biol Chem, vol. 285, pp. 19051-19059, 2010.
Yao et al., SIRT1 protects against emphysema via FOXO3-mediated reduction of premature senescence in mice, J Clin Invest, vol. 122(6), pp. 2032-2045, 2012.
Yeung et al., Modulation of NF-κB-dependent transcription and cell survival by the SIRT1 deacetylase, EMBO J, vol. 23(12), pp. 2369-2380, 2004.
Yuen et al., Angiogenic Dysfunction in Bone Marrow-Derived Early Outgrowth Cells from Diabetic Animals is Attenuated by SIRT1 Activation, Stem Cells Transl Med, vol. 1(12), pp. 921-926, 2012.
International Search Report of related PCT/US2015/62588, dated Feb. 23, 2016, 12 pages.

* cited by examiner

FIG. 1A
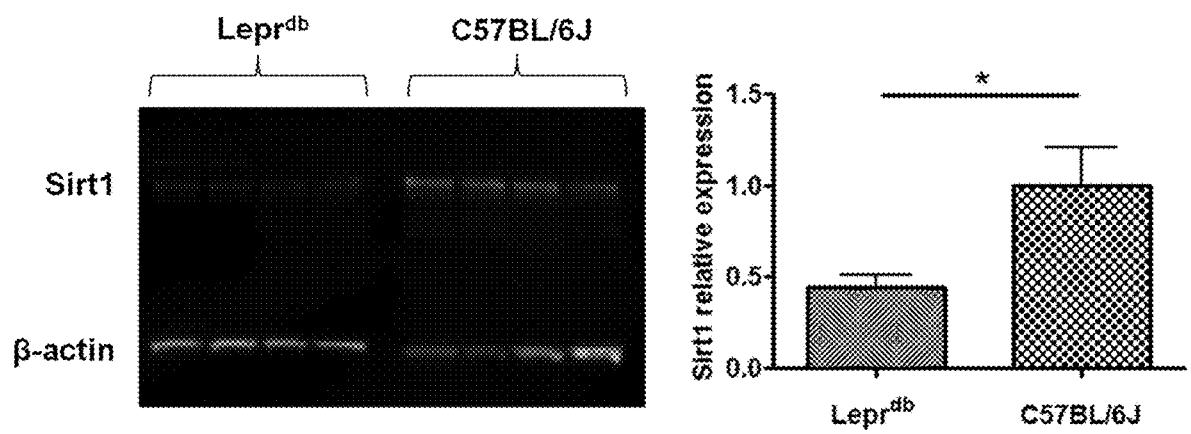
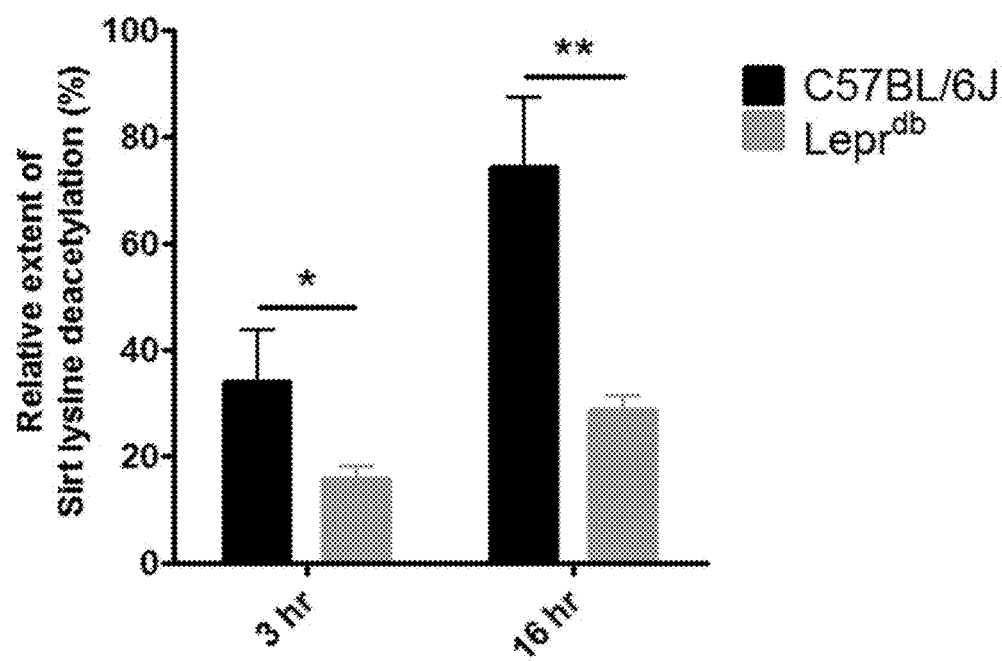
FIG. 1B

FIG. 2A
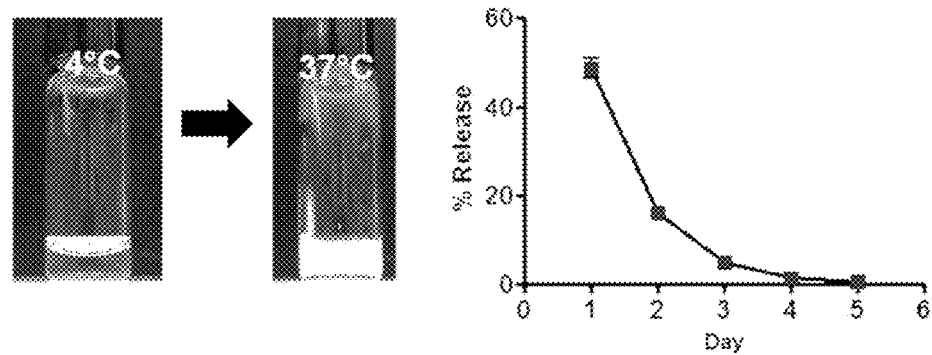
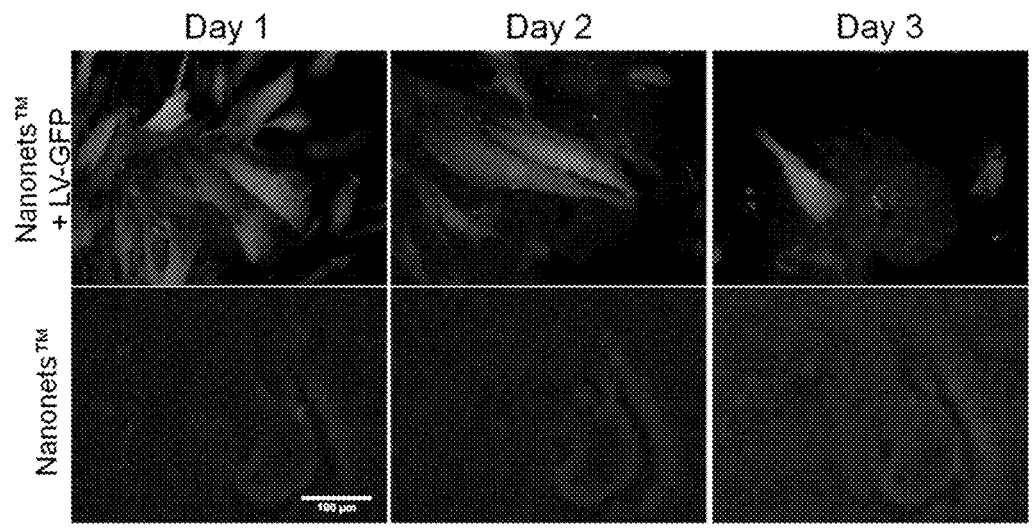
FIG. 2B

FIG. 3A
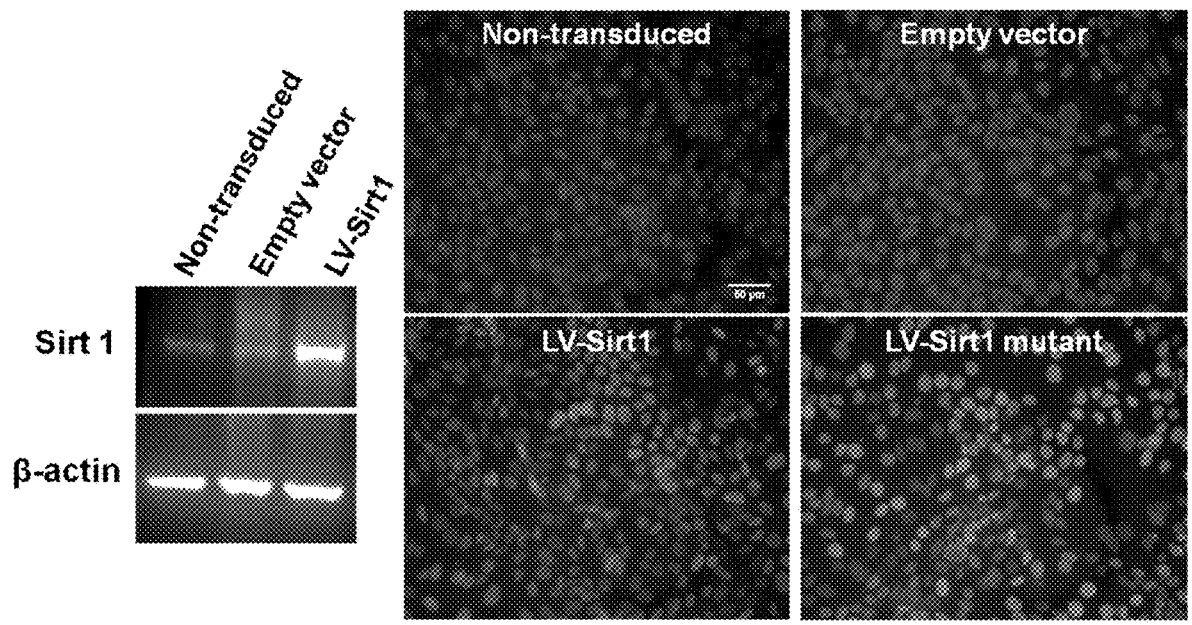
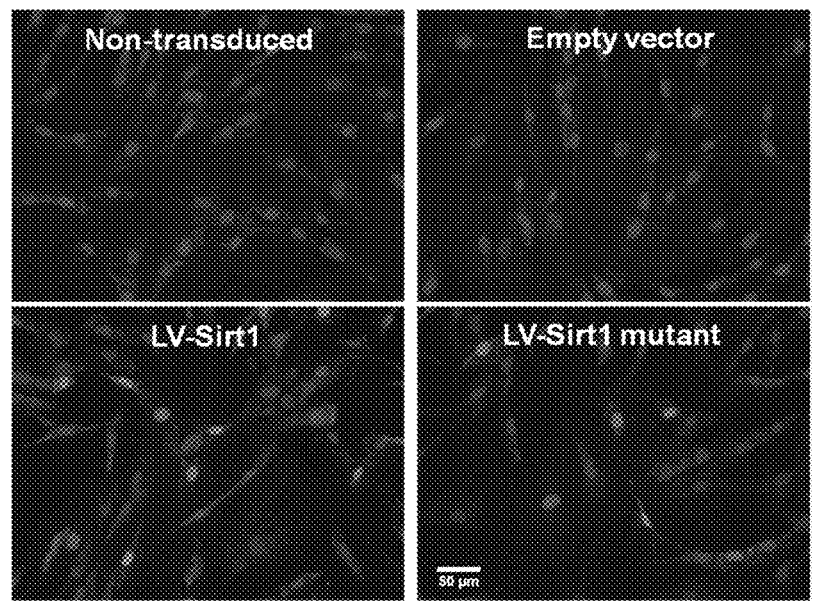
FIG. 3B

WOUND HEALING THROUGH SIRT1 OVEREXPRESSION

CROSS REFERENCE TO RELATED APPLICATIONS

The present invention is a divisional of U.S. patent application Ser. No. 15/529,288, filed May 24, 2017, now allowed, which is a § 371 U.S. National Entry of PCT/US2015/062588, filed Nov. 25, 2015, which claims priority to U.S. Provisional Patent Application 62/084,375, filed Nov. 25, 2014, each of which is incorporated by reference in its entirety.

SEQUENCE LISTING

The text of the computer readable sequence listing filed herewith, titled "32428-US-2-PCT_ST25", created Jul. 22, 2020, having a file size of 12,000 bytes, is hereby incorporated by reference in its entirety.

FIELD

Compositions and methods are provided for improved wound healing. In particular, provided herein are compositions and methods for the direct delivery of Sirtuin-1 (Sirt1) or vectors encoding Sirt1 to a wound (e.g., of a diabetic patient).

BACKGROUND

Diabetes-impaired wound healing remains a major clinical complication. A major complication associated with diabetes is impaired wound healing or chronic ulcers. Many molecular and physiological factors contribute to the impairment in diabetic wound healing. For instance, lack of angiogenesis or irregular blood vessel network, excessive and prolonged inflammation, rampant oxidative stress, and senescence are commonly cited.[1-5; herein incorporated by reference in their entireties]. Therefore, therapies that can modulate these events are crucial in improving wound healing.

Sirtuin-1 (Sirt1), an NAD+-dependent lysine deacetylase, has been shown to regulate and restore angiogenic function and the secretion of proangiogenic factors in diabetic endothelial progenitor cell (EPC).[6, 7; herein incorporated by reference in their entireties] Seminal papers have demonstrated that Sirt1 is involved in the protection against excessive inflammation and oxidative stress by deacetylating NFκB and Forkhead box O transcription factors.[8, 9; herein incorporated by reference in their entireties] Furthermore, Sirt1 inhibits cellular senescence, promotes keratinocyte differentiation, and protects against UV-induced DNA damage.[10-13; herein incorporated by reference in their entireties] Several studies have demonstrated that Sirt1 is downregulated or dysfunctional in a diabetic milieu and that Sirt1 overexpression improves glucose intolerance and insulin sensitivity and protects against diabetes.[14-19; herein incorporated by reference in their entireties] However, the role of Sirt1 in diabetic foot ulcers or wound healing is not known.

SUMMARY

Compositions and methods are provided for improved wound healing. In particular, provided herein are compositions and methods for the direct delivery of Sirtuin-1 (Sirt1) or vectors encoding Sirt1 to the wounds (e.g., of diabetic patients).

In some embodiments, provided herein are therapeutic devices comprising: (a) a vector encoding Sirtuin-1 (Sirt1); and (b) a hydrogel carrier. In some embodiments, the vector comprises a viral vector comprising a polynucleotide sequence encoding Sirt1. In some embodiments, the vector comprises a non-viral vector comprising a polynucleotide sequence encoding Sirt1. In some embodiments, the viral vector is a lentiviral vector or adeno-associated virus vector. In some embodiments, the hydrogel carrier is a biodegradable antioxidant and thermoresponsive hydrogel.

In some embodiments, provided herein are methods of treating a wound of a diabetic subject comprising administering a therapeutic device described herein to said subject. In some embodiments, the therapeutic device is administered directly to the wound. In some embodiments, the device comprises a bandage or dressing.

In some embodiments, provided herein are compositions comprising a nucleic acid comprising a Sirt1 gene and a biocompatible polymeric carrier material. In some embodiments, the Sirt1 gene is a transgene. In some embodiments, the nucleic acid is embedded within the carrier material. In some embodiments, the nucleic acid is coated onto the carrier material. In some embodiments, the nucleic acid is released from the carrier when the carrier contacts an aqueous or physiologic environment. In some embodiments, the carrier degrades when it contacts an aqueous or physiologic environment. In some embodiments, the carrier comprises a polymeric network or hydrogel. In some embodiments, the carrier comprises a polyester, polyurethane, polycarbonate, polyanhydride, polyphosphoester, or a mixture thereof. In some embodiments, the carrier comprises a citric acid polyester. In some embodiments, the carrier comprises poly(polyethyleneglycol co-citric acid-co-N isopropylacrylamide) (PPCN). In some embodiments, the Sirt1 gene is a synthetic sequence comprising at least 70% sequence identity (e.g., 70%, 75%, 80%, 85%, 90%, 95%, 100%, or ranges there between) with all or a portion of SEQ ID NO: 1. In some embodiments, the Sirt1 gene is a synthetic sequence and encodes a Sirtuin 1 polypeptide having at least 70% sequence identity (e.g., 70%, 75%, 80%, 85%, 90%, 95%, 100%, or ranges there between) with all or a portion of SEQ ID NO: 2. In some embodiments, the Sirt1 gene encodes an active Sirtuin 1 polypeptide (e.g., an active synthetic version of sirtuin 1).

In some embodiments, provided herein are compositions (e.g., carrier materials) comprising poly(polyethyleneglycol co-citric acid-co-N isopropylacrylamide) (PPCN).

In some embodiments, provided herein are methods of promoting wound healing comprising administering a Sirt1 gene to the wound under conditions that allow for overexpression of the Sirt1 gene at the wound site. In some embodiments, the Sirt1 gene is in an expression vector (e.g. AAV, lentivirus, non-viral vector, etc.). In some embodiments, the Sirt1 gene is on or within a carrier material. In some embodiments, the Sirt1 gene is released from the carrier material when the carrier contacts an aqueous or physiologic environment. In some embodiments, the carrier material degrades when it contacts an aqueous or physiologic environment. In some embodiments, the carrier material comprises a polymeric network or hydrogel. In some embodiments, the carrier material comprises a polyester, polyurethane, polycarbonate, polyanhydride, polyphosphoester, or a mixture thereof. In some embodiments, the carrier material comprises a citric acid polyester. In some embodiments, the carrier material comprises poly(polyethyleneglycol co-citric acid-co-N isopropylacrylamide) (PPCN). In some embodiments, the Sirt1 gene is a synthetic sequence comprising at least 70% sequence identity with all or a portion of SEQ ID NO: 1. In some embodiments, the Sirt1 gene is a synthetic sequence and encodes a Sirtuin 1 polypeptide having at least 70% sequence identity with all or a portion of SEQ ID NO: 2. In some embodiments, the Sirt1 gene encodes an active Sirtuin 1 polypeptide (e.g., an active synthetic version of sirtuin 1).

In some embodiments, provided herein are wound dressings comprising a dressing material for covering a wound of a subject and a wound contacting surface comprising a polymeric material with a Sirt1 gene embedded within the polymeric material, wherein upon application of the wound dressing to the wound, the Sirt1 gene is released from the polymeric material into the wound and expressed in cells within and surrounding the wound.

In some embodiments, provided herein is the use of a wound dressing or composition comprising a sirt1 gene embedded within a polymeric carrier material for the promotion of wound healing.

BRIEF DESCRIPTION OF THE DRAWINGS

FIGS. 1A-B. Decreased Sirt1 expression and sirtuin deacetylase activity in diabetic skin of mice. A: Immunoblot for Sirt1 and quantification of relative Sirt1 expression demonstrates that diabetic mice have approximately half the level of Sirt1 expression compared to healthy mice (n=7, mean±SEM). B: Sirtuin deacetylase activity is significantly lower in the skin of diabetic mice. Acetylated-lysine peptides were incubated with whole skin tissue lysates for either 3 hr or 16 hr and subsequently immobilized onto maleimide-terminated self-assembled monolayers. The monolayers were analyzed using mass spectrometry to quantify the fraction of acetylated- and deacetylated-lysine peptides (n≥9, mean±SEM).

FIGS. 2A-C. Lentiviruses are entrapped and released from PPCN. A: PPCN in the liquid form was mixed with lentiviruses and gelled at 37□C. Lentiviral particles released from PPCN were quantified over five days. Lentiviral particles were primarily released in the first three days (n=4, mean±SEM). B: GFP+ HDFs that were incubated with LV-GFP releaseate collected from PPCN between days 1 to 3 (scale bar=100 µm). C: Bioluminescence imaging of rats was measured over 6 weeks following subcutaneous injections of PPCN containing luciferase lentiviruses (LV-Luc) in the anterior left (AL) and posterior right (PR) regions. PPCN without any lentiviruses served as a control and were subcutaneously injected in the anterior right (AR) and posterior left (PL) (n=4, mean±SEM, *p<0.05).

FIGS. 3A-B. HEKa and HDF transduced to overexpress Sirt1 or Sirt1 mutant. Immunofluorescence and immunoblot images of Sirt1 or Sirt1 mutant overexpression in HEKa (A) and HDF (B) upon transduction with LV-Sirt1 or LV-Sirt1 mutant (scale bar=50 µm).

DEFINITIONS

Figure 2C:
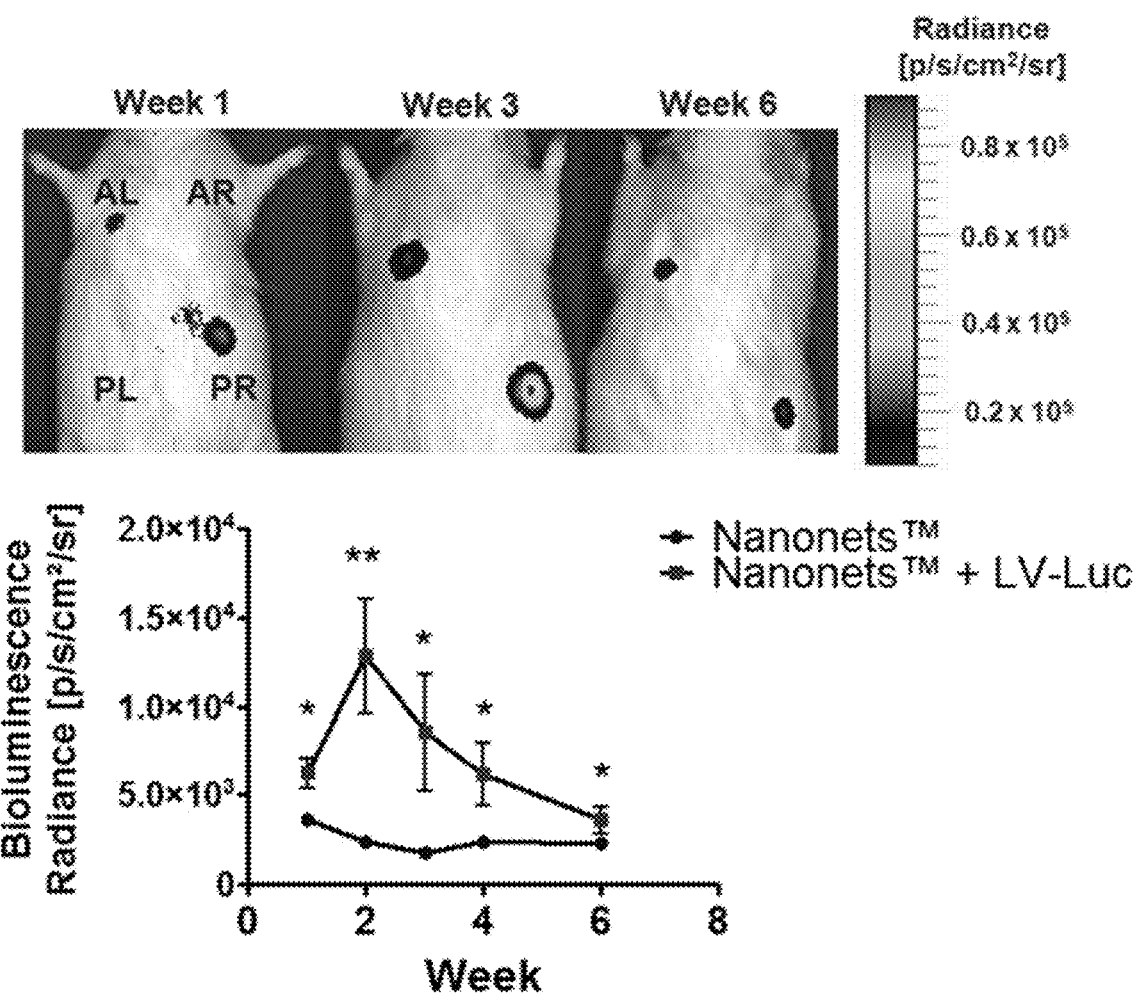

As used herein, the term "wound" refers to an injury to the dermis of the skin of a subject in which skin is torn, cut, punctured, or otherwise damaged or removed. Wounds typically include open wounds such as incisions, cuts, lacerations, abrasions, puncture wounds, traumatic skin injury, penetration wounds, burns, and the like. Wounds may be "chronic", for example, resulting from or exacerbated by disease (e.g., diabetes) or other slow tissue damage, or "acute", for example, resulting from an accident, injury, or surgical procedure.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

As used herein, the term "polypeptide" refers a polymer of amino acids linked together by peptide bonds. In some embodiments, polypeptides under about 50 amino acids or less in length are referred to herein as peptides. A polypeptide may comprise natural amino acids, non-natural amino acids, amino acid analogs, and/or modified amino acids. A peptide may be a subsequence of naturally occurring protein or a non-natural (synthetic) sequence.

As used herein, the term "mutant polypeptide" refers to a variant of a peptide having a distinct amino acid sequence from the most common variant occurring in nature, referred to as the "wild-type" sequence. A mutant polypeptide may be all or a subsequence of a mutant protein or polypeptide (e.g., a subsequence of a naturally-occurring protein that is not the most common sequence in nature), or may be a polypeptide that is not a subsequence of a naturally occurring protein or polypeptide. For example, "mutant Sirtuin 1" may be a a naturally-occurring, version of Sirtuin 1 that is distinct from the most common, wild-type version, or may be distinct sequence not found in naturally-occurring Sirtuin 1 proteins.

As used herein, the term "synthetic polypeptide" refers to a polypeptide having a distinct amino acid sequence from those found in natural polypeptide and/or proteins. A synthetic polypeptide is not a subsequence of a naturally occurring protein, either the wild-type (i.e., most abundant) or mutant versions thereof. For example, a "synthetic Sirtuin 1" is not a subsequence of naturally occurring Sirtuin 1. A "synthetic polypeptide," as used herein, may be produced or synthesized by any suitable method (e.g., recombinant expression, chemical synthesis, enzymatic synthesis, transfection, etc.).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a polypeptide with another amino acid within the same class.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "biocompatible" refers to materials and agents that are not toxic to cells or organisms at relevant concentrations. In some embodiments, a substance is considered to be "biocompatible" if its addition to cells in vitro results in less than or equal to approximately 10% cell death, usually less than 5%, more usually less than 1%. In The term "biodegradable", as used to describe the polymers, hydrogels, and/or wound dressings herein, refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "hydrogel" refers to a three-dimensional (3D) crosslinked network of hydrophilic polymers that swells, rather than being dissolved, in water.

As used herein, the term "thermoresponsive" refers to materials that exhibit altered physical characteristics at different temperature ranges. Particularly relevant herein are "phase-transitioning thermoresponsive" materials. Phase-transitioning thermoresponsive materials are soluble or in a liquid state at a first temperature range (e.g., below 26° C.) and insoluble or in a solid state at a second temperature range (e.g., 30-45° C.). A non-limiting example of a phase-transitioning thermoresponsive polymer is poly(N-isopropylacrylamide) (PNIPAM). Under standard conditions of neutral pH and in the absence of ionic species, PNIPAM undergoes a phase transition from liquid to solid at about 32° C.

DETAILED DESCRIPTION

Compositions and methods are provided for improved wound healing. In particular, provided herein are compositions and methods for the direct delivery of Sirtuin-1 (Sirt1) or vectors encoding Sirt1 to the wounds (e.g., of diabetic patients).

In some embodiments, provided herein are methods and compositions for administering Sirt1 to a wound (e.g., of a healthy subject, or a diabetic subject, etc.) to promote wound healing. In some embodiments herein, Sirtuin-1 or Sirt1 (or a vector encoding Sirt1) is embedded within, or applied to the surface a wound dressing or a coating thereof. The wound dressing is applied to a wound on a subject and the Sirtuin-1 or Sirt1 (or a vector encoding Sirt1) is released from the dressing and/or released upon biodegradation of the dressing. Experiments conducted during development of embodiments herein demonstrate that delivery of Sirt1 (e.g., from a wound dressing) and expression thereof promotes wound healing.

Experiments were conducted during development of embodiments herein to assess whether Sirt1 is differentially expressed in the skin of diabetic mice versus healthy controls and to determine whether Sirt1 overexpression in the wound bed, for example, effected through an antioxidant thermoresponsive dressing containing lentiviral vectors encoding for Sirt1 (LV-Sirt1), improves wound healing and tissue remodeling. In exemplary experiments, the thermoresponsive dressing used, referred to as PPCN, has intrinsic antioxidant properties due to the polyethylene-glycol-citrate oligomers in the polymer network [20; herein incorporated by reference in its entirety]. It undergoes reversible liquid to gel state transition at physiological temperatures allowing the gel to conform to the shape of the wound bed. PPCN also facilitates new tissue ingrowth. Experiments conducted during development of embodiments herein demonstrate that Sirt1, and a delivery vehicle, for example PPCN, are useful, for example, for treating chronic diabetic foot ulcers and other wound healing problems (e.g., associated with diabetes).

Impaired dermal wound healing, commonly associated with diabetes, increase the risk of infection, necrosis and eventually limb amputation. Sirt1 is downregulated or dysfunctional in a diabetic milieu and that Sirt1 overexpression improves glucose intolerance and insulin sensitivity and protects against diabetes.[14-19; herein incorporated by reference in their entireties]; however, whether Sirt1 is differentially expressed in diabetic versus healthy dermal tissue was unknown. Experiments conducted during development of embodiments herein demonstrate that the Sirt1 expression and Sirt lysine deacetylase activity are significantly reduced in the skin of diabetic mice when compared to healthy animals. SAMDI, a label-free quantitative method, was used to study Sirt lysine deacetylase activity in skin. Other technologies that probe enzyme activity rely on assays that use labeled substrates. Such substrates may interfere with enzyme activity [25, 26; herein incorporated by reference in their entireties]. Conversely, SAMDI mass spectrometry requires no labeling as mass spectrometry measures the mass-to-charge ratio of the desired analyte. Using SAMDI mass spectrometry, the ratio of deacetylated and acetylated peptide (GRK$^{ac}$HYC, a peptide with high specificity for Sirt) [22; herein incorporated by reference in its entirety] was determined to be significantly lower in lysate of diabetic dermal tissue.

A reduction in Sirt1 expression or activity has been linked to an increase in inflammatory markers. [27; herein incorporated by reference in its entirety] Sirt1 was demonstrated to attenuate inflammation by deacetylating the RelA/p65 component of NFκB.[8; herein incorporated by reference in its entirety] As the delay in diabetic wound healing has been widely attributed to excessive and chronic inflammation, this may be in part due to the lower Sirt1 expression in the skin of diabetic animals [2; herein incorporated by reference in its entirety]. Other studies demonstrate that Sirt1 overexpression in adipose tissue, macrophages, and pancreatic β-cells suppressed NFκB signaling and decreased inflammation.[27-29; herein incorporated by reference in its entirety] Experiments conducted during development of embodiments herein demonstrate that Sirt1 overexpression via lentiviruses encoding for Sirt1 (LV-Sirt1) at the wound bed accelerated diabetic wound healing. Histological analyses demonstrate that inflammation is dampened in LV-Sirt1-treated wounds.

The safe and efficient delivery of therapeutics to the wound is an important consideration that is often overlooked in the quest to identify the optimal target(s) to improve skin wound healing. Currently, there is only one FDA-approved product that relies on the release of a bioactive protein to improve the healing of diabetic foot ulcers—Regranex. Regranex's active ingredient, becalpermin, is a recombinant human platelet-derived growth factor homodimer that can easily be degraded by proteolytic enzymes in wound exudates and requires multiple wound applications to maintain therapeutic levels.[30; herein incorporated by reference in its entirety] This therapy leads to modest improvements in wound closure rates but at the expense of a higher risk of cancer.[31; herein incorporated by reference in its entirety] Alternatively, the delivery of a transgene or the overexpression of a target gene in the wound bed has its advantages in that long-term therapeutic exposure can be achieved without the need for storing and releasing large quantities of a therapeutic protein and incurring the high protein production costs.

In some embodiments, provided herein are compositions, devices and methods of use thereof for treating wounds of a subject (e.g., a diabetic patient) with more rapid and improved results over existing techniques. In some embodiments, devices comprise a mechanism for delivery and/or release of Sirt1 (e.g., diffusion from a device material, degradation of a device material, etc.). Sirt1 may be delivered as a protein (Siruin1) or as a nucleic acid encoding Sirt1. Full-length Sirt1 may be delivered or an active fragment thereof may be delivered. When delivered as a nucleic acid, Sirt1 may be within a suitable vector. A vector may be viral (e.g., lentivirus, AAV, etc.) or non-viral (e.g., plasmid, bacmid, etc.). In some embodiments, in addition to Sirt1, a vector further comprises elements to allow/promote expression of Sirt1.

In some embodiments, a device further comprises additional agents for promotion of wound healing (e.g., agents specific to diabetic wounds, agents for general wound healing. Such agents include, but are not limited to antiseptics, antibiotics, analgesics, narcotics, clotting agents, etc.

In some embodiments, a device comprises a bandage, dressing material, patch, etc. coated or impregnated with a liquid, hydrogel, powder, paste, lotion, etc. comprising the Sirt1 (protein or nucleic acid). In some embodiments, a device is a liquid, hydrogel, powder, paste, lotion, etc. comprising the Sirt1 (protein or nucleic acid).

In some embodiments, methods of wound treatment comprise administering a device described herein to a wound of a subject with diabetes. In some embodiments, a dressing is changed regularly (e.g., hourly, semi-daily, daily, weekly, monthly, etc.). In some embodiments, methods described herein are employed along with other wound and/or diabetes treatments understood in the art.

In some embodiments, provided herein are biodegradable, bioactive polymers or hydrogels that comprise wound dressings, implantable compositions, and coatings (e.g., for medical devices) that promote wound healing. In some embodiments, gene-delivery vectors are coated onto or dispersed or embedded within a polymer or hydrogel matrix for delivery to a wound site by interaction with and/or secretion into the wounded tissue to promote tissue restoration. In addition, the polymers can be loaded with various bioactive agents that either attract or hold the precursor cells within the polymer matrix or promote the natural healing process in a wound, such as a chronic wound.

In some embodiments, gene delivery vectors and/or other bioactive agents (e.g., for the promotion or wound healing, antibiotics, antiseptic, anti-inflammatory, etc.) elute from the wound dressing and/or polymer for delivery to the wound. In other embodiments, as the hydrogels or polymers of the dressing biodegrade, gene delivery vectors and/or other bioactive agents are released into and/or onto the wound tissue. In some embodiments, depending upon the rate of biodegradation of the polymer or hydrogel (e.g., which can be controlled via the particular materials used), the rate of delivery and the longevity of the dressing is controlled.

Provided herein are compositions, materials, dressings, devices, etc. for the delivery of Sirt1 and Sirt1-expressing vectors to wounds and surrounding cells/tissues for the promotion of wound healing. Suitable materials finding use in the Sirt1 delivery compositions described herein in include polymers, hydrogels, thermosets, polymer matrices, etc. In some embodiments, materials comprise combinations of the forgoing. In some embodiments, a material is provided upon which (e.g., coated onto), or within which (e.g., embedded within) a nucleic acid encoding Sirt1 (e.g., within an expression vector) is carried (e.g., a carrier material). In some embodiments, a polymeric matrix is provided as a carrier material for a Sirt1 nucleic acid (e.g., within an expression vector and/or other carrier (e.g., liposome, etc.).

In some embodiments, a polymeric matrix is provided. In some embodiments, the matrix comprises branched and/or crosslinked polymers (e.g., a single polymer species, multiple different crosslinked and/or branch polymers). In some embodiments, materials comprise networks (e.g., crosslinked, branched, non-covalent, etc.) of polymers, at suitable polymer densities and crosslink densities to achieve desired properties (e.g., physical properties of the material (e.g., strength, flexibility, density, mass, adhesion, etc.), elution of bioactive agent (e.g., Sirt1 vector), degradation rate, thermoresponsiveness, etc.).

In some embodiments, a carrier material is one or more of (e.g., all) biodegradable (e.g., degrades (e.g., chemically, enzymatically, hydrolytically, etc.) into monomer components when exposed to aqueous and/or physiologic conditions), biocompatible (e.g., neither the material or its degradation products are substantially toxic to cells or living organisms at relevant concentrations), thermoresponsive (e.g., liquid to solid phase transitioning at 25°, 26°, 27°, 28°, 29°, 30°, 31°, 32°, 33°, 34°, 35°, 36°, 37°, 38°, 39°, etc.), flexible, moldable, etc.

In some embodiments, a carrier material is a biocompatible polymeric matrix. In some embodiments, a biocompatible polymeric matrix can comprise a polyester, polyurethane, polycarbonate, polyanhydride, polyphosphoester, or a mixture thereof. In some embodiments, the biocompatible polymeric matrix is elastomeric. In some embodiments, the biocompatible polymeric matrix is a hydrogel.

In some embodiments, carrier materials comprise a hydrogel, or a formulation of hydrophilic cross-linked polymers. Examples of hydrogels that are commercially available for medical indications include: GELIPERM (Geistlich-Pharma/Fougera), GELIPERM (Geistlich-Pharma/Fougera), VIGILON (Bard), Bard ABSORPTION DRESSING (Bard), CUTINOVA GELFILM (Biersdorf), ELASTO-GEL (Southwest Technologies), AQUASORB (DeRoyal), CARRADRES (Carrington Laboratories Inc.), 2NDSKIN (Spenco Medical Ltd), DERMA-GEL (Medline Industries), FLEXDERM (Dow Hickman Pharmaceuticals Inc.), ACRYDERM (AcryMed), THINSITE TRANSORBENT (B. Braun), CLEARSITE (Conmed Corporation), CURAGEL (Kendall) and NU-GEL (Johnson & Johnson). In some embodiments, other hydrogels made from the crosslinking of polymers also find use herein).

Suitable polymers that may find use in embodiments herein (e.g., in the formation of a hydrogel, crosslinked with another polymer, within a composite of multiple materials) include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly (octanediol citrate), etc.), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties).

In some embodiments, any molecular entities capable of reacting with the reactive groups of, for example, citric acid, polyethylene glycol, or the other monomers and polymers described herein, may find use in the generation of polymeric compositions and networks thereof within the scope of the embodiments described herein. For example, additional monomer groups for use in embodiments herein include, but are not limited to: a lactide (e.g., D-lactide, L-lactide, or D,L-lactide), glycolide, lactone, carbonate, thiocarbonate, oxaketocycloalkane, thiooxaketocycloalkane, polyethylene glycol, glycerol, linear aliphatic diol (e.g., butanediol, hexanediol, octanediol, decanediol, dodecanediol, and shorter or longer linear aliphatic diols), linear aliphatic diacid (e.g., succinic acid, glutaric acid, adipic acid, pimelic acid, suberic acid, azelaic acid, sebacic acid, dodecanedioic acid, and shorter or longer linear aliphatic diacids), citric acid, isocitric acid, aconitic acid, propane-1,2,3-tricarboxylic acid, trimesic acid, diols, triols, polyols, itaconic acid, maleic acid, maleic anhydride, glycerol 1,3-diglycerolate diacrylate, glycerol dimethacrylate, 3-(acryloyloxy)-2-hydroxypropyl methacrylate, N-isopropylacrylamide, etc.

In certain embodiments, biocompatible polymeric matrix comprises a polyester, such as a poly(citric acid-diol), poly(glycerol-diacid), poly(polyethyleneglycol citrate) acrylate, poly(polyethyleneglycol co-citric acid-co-N isopropylacrylamide) (PPCN), etc.

In some embodiments, materials comprise at least one type of polymer comprising citric acid monomers polymerized with one or more additional monomer units (e.g., polyethylene glycol, aliphatic diol, etc.). In some embodiments, materials comprise a citric acid polyester. Citric acid is a reactive tricarboxylic acid that is part of the Krebs cycle and has been used as a key reactant monomer for the synthesis of polydiolcitrates and other citric acid polyesters with a wide range of properties and uses (Yang, J., et al., Synthesis and evaluation of poly(diol citrate) biodegradable elastomers. Biomaterials, 2006. 27(9): p. 1889-98.; U.S. Pat. Nos. 8,772,437; 8,758,796; 8,580,912; 8,568,765; U.S. Pub. No. 2014/0155516; U.S. Pub. No. 2014/0135407; herein incorporated by reference in their entireties). Depending on the choice of monomers polymerized with citric acid, materials are achieved with controllable elasticity, biodegradability, and antioxidant properties can be developed (Serrano et al. Adv Mater, 2011. 23(19): p. 2211-5.; Yang J., et al., A thermoresponsive biodegradable polymer with intrinsic antioxidant properties. Biomacromolecules, 2014. 15(11):3942-52.; U.S. Pub. No. 2014/0037588; herein incorporated by reference in its entirety).

In some embodiments, a biocompatible polymer or network thereof comprises one or more diol monomers. In polymers and materials comprising diol monomers, any suitable diols may be selected for use. Examples of diols include, but are not limited to, aromatic-diols (e.g., hydroquinone, catechol, resorcinol), C2-C20 alkyl-diols, C2-C20 alkenyl-diols (e.g., tetradeca-2,12-diene-1,14-diol), and mixtures thereof. The diols may also include substituents as well. Reactive groups like amines and carboxylic acids will increase the number of sites available for cross-linking Amino acids and other biomolecules will modify the biological properties of the polymer. Aromatic groups, aliphatic groups, and halogen atoms will modify the inter-chain interactions within the polymer. Diols further include macromonomer diols such as polyethylene oxides, and N-methyldiethano amine (MDEA). In certain embodiments, the diol comprises one or more C2-C20 alkyl-diols, C2-C20 alkenyl-diols, or mixtures thereof. In certain other embodiments, the diol comprises one or more C2-C20 alkyl-diols, such as a C6-C20 alkyl-diol, or a C6-C14 alkyl-diol, or a C6-C12 alkyl-diol. For example, the diol can comprise an alkanediol, such as 1,12-dodecanediol, 1,10-decanediol, 1,8-octanediol, or a mixture thereof. In another example, the diol can comprise 1,10-decanediol, 1,8-octanediol, or a mixture thereof. In another example, the diol can comprise 1,8-octanediol (e.g., the polyester is poly(1,8-octanediol-citrate).

Polymers herein may be crosslinked, for example, by optionally including one or more hyperbranching monomers, such as a monomer comprising three alcohol functional groups (a "triol"), in order to control the degradation thereof. For example, glycerol can be added in addition to the citric acid and diol monomer (0-3 mol %, provided the molar ratio of carboxyl and hydroxyl group among the three monomers was maintained as 1/1). Glycerol is a hydrophilic component, and its addition can facilitate the water penetration into the network films which results in the faster degradation rate. Increasing amounts of glycerol can increase the break strength and Young's modulus of the resulting polyester. For example, the Young's modulus can range from 1 to 16 MPa, with strengths and strains at break of up to 10 MPa and 500%, respectively. Depending on the synthesis conditions, total degradation time may range from months to years. Degradation within 6 to 12 months is preferred.

In some embodiments, materials comprise a poly(glycerol-diacid). A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid)s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), C2-C20 alkyl-diacids, C2-C20 alkenyl-diacids, and mixtures thereof. The diacids may also include substituents as well. Reactive groups like amine and hydroxyl will increase the number of sites available for cross-linking Amino acids and other biomolecules will modify the biological properties of the polymer. Aromatic groups, aliphatic groups, and halogen atoms will modify the inter-chain interactions within the polymer.

In some embodiments, carrier materials comprise polymers of citric acid, polyethylene glycol, and glycerol 1,3-diglycerolate diacrylate. In some embodiments, citric acid, polyethylene glycol, and glycerol 1,3-diglycerolate diacrylate are polymerized to form a polymer (e.g., pre-polymer) of poly(polyethyleneglycol citrate) acrylate (PPCac). In some embodiments, carrier materials comprise polymers of citric acid, polyethylene glycol, glycerol 1,3-diglycerolate diacrylate, and N-isopropylacrylamide (NIPAAm). In some embodiments, PPCac and NIPAAm are reacted together to produce a poly(polyethyleneglycol citrate co N-isopropylacrylamide) (PPCN) polymer. In some embodiments, PPCN is provided as a carrier material.

In some embodiments, polymers herein (e.g., PPCN or another polymer) comprise at least 0.1% citric acid monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% citric acid monomers (e.g., <99%, <98%, <95%, <90%, <80%, <70%, <60%, <50%, <40%, <30%, <20%,<10%, <5%,<4%, <3%, <2%, <1%, <0.5%,). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% citric acid monomers.

In some embodiments, polymers herein (e.g., PPCN or another polymer) comprise at least 0.1% polyethylene glycol monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% polyethylene glycol monomers (e.g., <99%, <98%, <95%, <90%, <80%, <70%, <60%, <50%, <40%, <30%, <20%, <10%, <5%,<4%, <3%, <2%, <1%, <0.5%,). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% polyethylene glycol monomers.

In some embodiments, polymers herein (e.g., PPCN or another polymer) comprise at least 0.1% glycerol 1,3-diglycerolate diacrylate monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% glycerol 1,3-diglycerolate diacrylate monomers (e.g., <99%, <98%, <95%, <90%, <80%, <70%, <60%, <50%, <40%, <30%, <20%,<10%, <5%,<4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% glycerol 1,3-diglycerolate diacrylate monomers.

In some embodiments, polymers and materials herein (e.g., PPCN or another polymer) comprise at least 0.1% N-isopropylacrylamide monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% N-isopropylacrylamide monomers (e.g., <99%, <98%, <95%, <90%, <80%, <70%, <60%, <50%, <40%, <30%, <20%,<10%, <5%,<4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% N-isopropylacrylamide monomers.

In some embodiments, provided herein are composites of the polymers, hydrogels, materials described herein (e.g., poly(polyethyleneglycol citrate co N-isopropylacrylamide (PPCN)) with additional components. For example, materials may be used with one or more biodegradable polymers to form a composite material.

In some embodiments, a PPCN composite material comprises at least 0.1% PPCN (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, a PPCN composite material comprises less than 99% PPCN (e.g., <99%, <98%, <95%, <90%, <80%, <70%, <60%, <50%, <40%, <30%, <20%,<10%, <5%,<4%, <3%, <2%, <1%, <0.5%). In some embodiments, a PPCN composite material comprises PPCN in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, about 0.5%, or ranges therein. The aforementioned percentages may be wt % or molar %.

Composites may also be made of PPCN (or other polymeric materials) and a non-biodegradable polymer, such as: silicone rubber, polyethylene, acrylic resins, polyurethane, polypropylene, and polymethylmethacrylate. Composites of PPCN and non-polymeric materials are also within the scope of embodiments described herein. Such non-polymer components include, but are not limited to a bioceramic (e.g., hydroxyapatite, tricalcium phosphate, etc.), nanoparticles (e.g., iron oxide, zinc oxide, gold, etc.), cosmetic ingredients (e.g., glycerin, glyceryl dilaurate, diisobutyl adipate, mineral oil, dimethicone, pentylene glycol, cyclopentasiloxane, etc.) and tattoo inks (e.g. glycerin, propylene glycol, etc.). In some embodiments, synthesis of the polymers, hydrogels, networks, etc. described herein are produced by combination of the component molecules (e.g., citric acid, polyethylene glycol and glycerol 1,3-diglycerolate diacrylate; PPCac and NIPAAm, etc.) under the appropriate conditions (e.g., temperature, pressure, pH, etc.). In some embodiments, reaction, crosslinking, polymerization, etc. occurs upon combination of the components under appropriate conditions in the absence of any additional enzyme or chemical catalysts. In some embodiments, a radical initiator (e.g., AIBN) is used to induce a reaction or polymerization.

In some embodiments, components (e.g., citric acid, polyethylene glycol and glycerol 1,3-diglycerolate diacrylate; etc.) are heated to at least 100° C. (e.g., 100° C., 110° C., 120° C., 130° C., 140° C., 150° C., 160° C., 170° C., 180° C., 190° C., 200° C., or more). In some embodiments, components (e.g., PPCac and NIPAAm, etc.) are heated to at least 40° C. (e.g., 40° C., 50° C., 60° C., 70° C., 80° C., 90° C., 100° C., 110° C., 120° C., or more). In some embodiments, components are reacted at a temperature not exceeding 250° C. (e.g., <240° C., <220° C., <200° C., <180° C., <160° C., or less).

In some embodiments, components (e.g., citric acid, polyethylene glycol and glycerol 1,3-diglycerolate diacrylate; PPCac and NIPAAm, etc.) are reacted for at least 1 minute (e.g., >1 minute, >2 minutes, >3 minutes, >4 minutes, >5 minutes, >10 minutes, >20 minutes, >30 minutes, >45 minutes, >1 hour, >2 hours, >3 hours, >4 hours, >12 hours, >24 hours, >48 hours, >72 hours, or more).

In some embodiments, citric acid, polyethylene glycol and glycerol 1,3-diglycerolate diacrylate are reacted at a ratio of 5:9:1, 5:8:2, 5:7:3, 5:6,4, 5:5:5, 4:9:2, 3:9:3, 2:9:4, 1:9:5, 6:8:1, 7:7:1, 8:6:1, 9:5:1, 10:4:1, 11:3:1, 12:2:1, 13:1:1, 4:10:1, 3:11:1, 2:12:1, 1:13:1, or any other suitable ratios thereof or rages there between. In some embodiments, PPCac and NIPAAm are reacted at a ratio of 10:1, 9:1, 8:1, 7:1, 6:1, 5:1, 4:1, 3:1, 2:1, 1:1, 1:2, 1:3, 1:4: 1:5, 1:6, 1:7, 1:8, 1:9, 1:10, or any other suitable ratios thereof or rages there between.

In some embodiments, a carrier material (e.g., biodegradable polymer) coated or embedded with a Sirt1-encoding nucleic acid (e.g., within a vector) is configured for application directly to a wound. In some embodiments, the conformational and adhesive properties of the carrier material allow for the material to stay in place upon application to the wound. In some embodiments, thermoresponsive properties of the carrier material allow for application of the carrier to the wound as a liquid (e.g., at room temperature) followed by gelling of the material upon temperature increase to physiologic conditions. In some embodiments, the carrier is shaped to fit on or within a wound. The carrier material may be applied in the form of an amorphous gel, a wafer, a thin sheet, etc. In some embodiments, an adhesive is applied to the carrier material (e.g., the boarders of the material) to assist in securing the carrier to the wound.

In some embodiments, the carrier material comprises or is applied to the wound-contacting face of a wound dressing. Suitable wound dressings include gauze, a bandage, a film dressing, a pad, membrane, etc. Suitable dressings that may be used in conjunction with embodiments herein (e.g., modified to have a wound-contacting face comprising a carrier material herein embedded with a Sirt1 nucleic acid) include, for example, those described in: U.S. Pat. No. 4,732,146 to Fasline et al., U.S. Pat. No. 4,917,112 to Kalt, U.S. Pat. No. 4,909,243 to Frank et al., U.S. Pat. No. 4,907,579 to Kum, U.S. Pat. No. 5,167,613 to Karami et al., U.S. Pat. No. 3,779,242 to McCullough, U.S. Pat. No. 4,709,695 to Kohn et al., U.S. Pat. No. 4,399,816 to Spangler, U.S. Pat. No. 5,086,763 to Hathman, and U.S. Pat. No. 4,926,883 to Strock, all of which is herein incorporated by reference in their entireties.

As used herein, the terms "Sirt1" and "Sirt1 gene" (which may be used interchangeably at times herein) generally refer to the nucleic acid encoding the Sirt1 miRNA, and sirtuin 1 protein, and homologues, orthologues, and variants thereof, including conservative, semi-conservative, and non-conservative substitutions, additions, and deletions not significantly adversely affecting the structure or function of Sequence variants of Sirt1 generally fall into one or more of three classes: substitutional, insertional or deletional variants. Insertions include 5' and/or 3' terminal fusions as well as intrasequence insertions of single or multiple residues. Insertions are also introduced within the mature sequence of Sirt1. These, however, ordinarily will be smaller insertions than those at the 5' or 3' terminus, on the order of 1 to 4 residues.

Insertional sequence variants of Sirt1 are those in which one or more residues are introduced into a predetermined site in the target Sirt1. Most commonly insertional variants are fusions of nucleic acids at the 5' or 3' terminus of Sirt1.

Deletion variants are characterized by the removal of one or more residues from the Sirt1 RNA sequence. These variants ordinarily are prepared by site specific mutagenesis of nucleotides in the DNA encoding Sirt1, thereby producing DNA encoding the variant, and thereafter expressing the DNA in recombinant cell culture. However, variant Sirt1 fragments may be conveniently prepared by in vitro synthesis. The variants typically exhibit the same qualitative biological activity as the naturally-occurring analogue, although variants also are selected in order to modify the characteristics of Sirt1.

Substitutional variants are those in which at least one residue sequence has been removed and a different residue inserted in its place. While the site for introducing a sequence variation is predetermined, the mutation per se need not be predetermined. For example, in order to optimize the performance of a mutation at a given site, random mutagenesis may be conducted at the target region and the expressed Sirt1 variants screened for the optimal combination of desired activity. Techniques for making substitution mutations at predetermined sites in DNA having a known sequence are well known. Nucleic acid substitutions may result in a Sirt1 gene may result in conservative, semi-conservative, or non-conservative substitutions to the Sirtuin 1 protein.

In some embodiments, a Sirt1 nucleic acid comprises at least 70% sequence identity (e.g., 70%, 75%, 80%, 85%, 90%, 95%, 96%, 97%, 98%, 99%, 100%, or ranges there between) with wild-type Sirt1 (SEQ ID NO: 1).

In some embodiments, a Sirt1 nucleic acid encodes a sirtuin 1 protein with at least 70% sequence identity (e.g., 70%, 75%, 80%, 85%, 90%, 95%, 96%, 97%, 98%, 99%, 100%, or ranges there between) with wild-type sirtuin 1 (SEQ ID NO: 2). In some embodiments, a Sirt1 nucleic acid comprises at least 40% sequence similarity (e.g., 40%, 45%, 50%, 55%, 60%, 75%, 70%, 75%, 80%, 85%, 90%, 95%, 96%, 97%, 98%, 99%, 100%, or ranges there between) with wild-type sirtuin 1 (SEQ ID NO: 2). In some embodiments, a synthetic sirtuin 1 protein is provided (e.g., encoded in a Sirt1 nucleic acid) having conservative, semi-conservative, and/or non-conservative substitutions with respect to wild-type sirtuin 1.

To enable cellular expression of the Sirt1 nucleic acids at a wound site, the Sirt1 gene is provided within or as a part of a nucleic acid expression construct. In some embodiments, an expression construct comprises at least a coding region for a Sirt1 gene (e.g., comprising SEQ ID NO:1 or variants thereof). In some embodiments, a nucleic acid construct further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence may find use herein. In some embodiments, the promoter is specific for the cell population at the wound site (e.g., dermal tissue cells). The nucleic acid construct may further include an enhancer, which can be adjacent or distant to the promoter sequence and can function in up regulating the transcription therefrom.

In some embodiments, the nucleic acid construct is, for example, a plasmid, a bacmid, a phagemid, a cosmid, a phage, a virus or an artificial chromosome.

In some embodiments, a nucleic acid construct for transfer into cells at the wound site and expression within those cells is a viral or non-viral constructs, such as adenovirus, lentivirus, Herpes simplex I virus, or adeno-associated virus (AAV), a lipid-based system, etc. Useful lipids for lipid-mediated transfer of the gene are, for example, DOTMA, DOPE, and DC-Chol [Tonkinson et al., Cancer Investigation, 14(1): 54-65 (1996); herein incorporated by reference in its entirety]. Useful viruses for viral transfer include adenoviruses, AAV, lentiviruses, or retroviruses. A viral construct such as a retroviral construct includes at least one transcriptional promoter/enhancer or locus-defining elements, or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence. The construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other non-viral vectors include cationic lipids, polylysine, and dendrimers.

As used herein, the terms "vector" and "expression vector" refers to a carrier molecule or agent into which a nucleic acid sequence is placed (e.g., inserted) for introduction into a cell where it can be replicated and/or expressed. In some embodiments, upon delivery into a cell, the nucleic acid molecules are transcribed into RNA and/or translated into a protein, polypeptide, or peptide. In some embodiments, expression vectors comprise one or more "control sequences" to regulate (e.g., induce, enhance, etc.) the transcription and/or translation of an operably linked coding sequence in a particular host cell. In some embodiments, a vector includes an origin of replication. In some embodiments, the vector facilitates integration of the vector or a coding sequence therein into the genome of a cell or organism. In some embodiments, a vector is, for example, a plasmid, a bacmid, a phagemid, a cosmid, a phage, a virus, or an artificial chromosome. In some embodiments, the vector is a viral vector (e.g., bacteriophage, mammalian virus, plant virus, etc.). In some embodiments, a viral vector is derived from a virus such as an adeno-associated virus, vaccinia virus, lentivirus, polio virus, hepatitis virus, papilloma virus, cytomegalovirus, simian virus, or herpes simplex virus.

In some embodiments, a Sirt1 nucleic acid construct (e.g., within a vector) is formulated for administration onto or into a wound. Therapeutic compositions for local and/or topical administration to a wound described herein may be formulated as solutions, emulsions, suspensions, or dispersions in suitable pharmaceutical bases or carriers, according to conventional methods known in the art for preparation of various dosage forms. For the topical applications described herein, compositions may be formulated as gels, creams, pastes, lotions, or ointments or as a similar vehicle suitable for topical administration. Topical administration may also be effected through the use of liposomal or other delivery systems.

Therapeutic compositions may be formulated for transdermal or interdermal delivery or in an extended release formulation. For example, suitable formulations may employ liposomes or similar lipid-based vesicles to enhance stability of the product or to provide for extended release to the affected area. Any suitable liposome or liposome composition may be employed. Exemplary liposomes include those described in U.S. Pat. Nos. 6,958,160 and 7,150,883 (herein incorporated by reference in their entireties), and may comprise one or more fatty acid-diacylglycerol-PEG derivatives such as PEG-12 glyceryl dioleate, PEG-23 glyceryl distearate, PEG-12 glyceryl dipalmitate, or PEG-12 glyceryl dimyristate. Other examples of suitable liposomes are those made from conventional phospholipids derived from egg lecithin or soy lecithin.

In some embodiments, a formulation comprises one or more pharmaceutically-acceptable excipients. A pharmaceutically acceptable excipient is a substance that is non-toxic and otherwise biologically suitable for administration to a subject. Such excipients facilitate administration of and are compatible with the wound-dressing and gene-delivery applications described herein. Examples of pharmaceutically acceptable excipients include stabilizers, thickeners, lubricants, surfactants, diluents, anti-oxidants, binders, preservatives, coloring agents (such as pigments or dyes), or emulsifiers. Pharmaceutical excipients may also include skin permeation enhancers. Stabilizers specifically include amine stabilizers. Suitable thickeners are the swelling agents customarily used for gel formation in galenic pharmacy. Examples of suitable thickeners include natural organic thickeners, such as agar-agar, gelatin, gum arabic, a pectin, and the like, modified organic natural compounds, such as carboxymethylcellulose or cellulose ethers, or fully synthetic organic thickeners, such as poly acrylic compounds, vinyl polymers, or poly ethers. In some embodiments, the excipient can increase the smoothness or other properties of a wound dressing formulation. Such additives include, but are not limited to glycerin, propylene glycol, butylene glycol, esters, diacyl glycerol esters, and starch. In certain embodiments, pharmaceutical compositions are sterile compositions.

In particular embodiments, the pharmaceutically acceptable excipient is purified water, ethanol, ethoxydiglycol, butylene glycol, carbopol ETD 2001, citric acid, isopropyl palmitate, caprilic/capric triglyceride, sorbitan stearate, corn oil, stearic acid, cetyl alcohol, glyceryl stearate, PEG-100 stearate, methylparaben, propylparaben, oleic acid, phenoxyethanol, carbopol Ultrez 10, glycerin, carbopol ETD 2020, propylene glycol, cholesterol, trolamine, ammonium acryloyldimethyltaurate/VP copolymer, or benzyl alcohol, or a mixture thereof.

The compositions, systems, and methods herein are not limited by the nature of the materials used to deliver Sirt1, unless otherwise indicated. However, in some embodiments, an expression vector comprising the Sirt1 gene is embedded within a PPCN-containing material on a wound dressing.

Exemplary experiments were conducted during development of embodiments herein to generate full-thickness dermal wounds in diabetic mice and delivered lentiviruses encoding for Sirt1 (LV-Sirt1) from an exemplary polymer material, PPCN. PPCN is an antioxidant and is thermo-responsive, being a liquid at lower temperatures (e.g., <25° C.) and gelling at increased temperatures (e.g., >30° C.). Wound closure rate was significantly faster in the PPCN+ LV-Sirt1 group compared to PPCN group. Furthermore, PPCN+LV-Sirt1 treatment had less dermal fibrosis, less inflammation, and faster regeneration of pilosebacious units. Experiments conducted during development of embodiments herein indicate that that Sirt1 overexpression (e.g., effected via PPCN) provides enhanced healing (e.g., in diabetic ulcers), and that release of Sirt1 from a polymer wound dressing is an effective method for enhancing wound healing.

Figure 7:
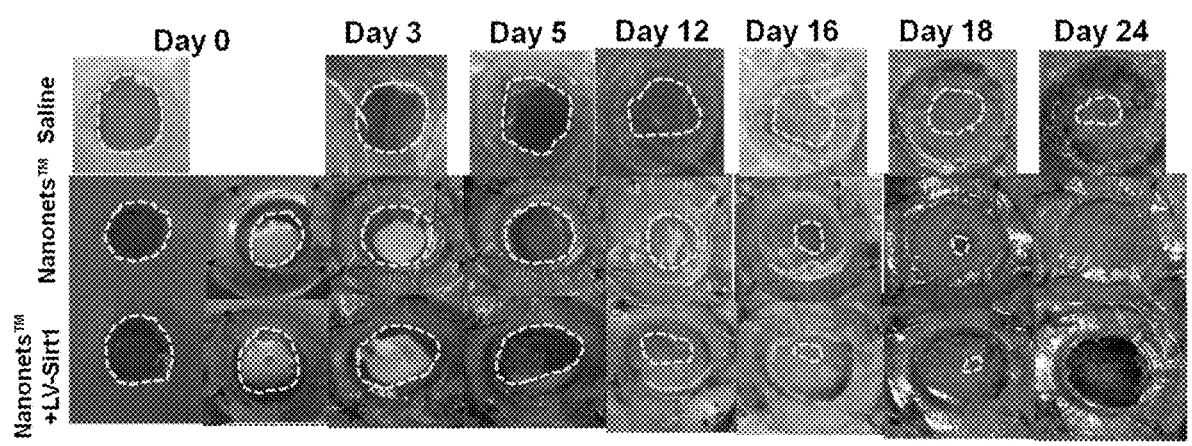
FIG. 7. PPCN+LV-Sirt1 and PPCN accelerate diabetes-impaired wound healing. A: Saline, PPCN, or PPCN+LV-Sirt1 treatments were randomly assigned to each full-thickness wound centered within sutured donut-shaped splits. Wound closure rates were expressed as a percentage of the closed wound area. PPCN-treated wounds have accelerated wound closure compared to saline-treated wounds, albeit slower than PPCN+LV-Sirt1-treated wounds. (n≥6, Mean±SEM) *P<0.05 PPCN+LV-Sirt1 vs PPCN; +P<0.05 PPCN+LV-Sirt1 vs Saline; ^P<0.01 PPCN vs Saline.
Figure 7:
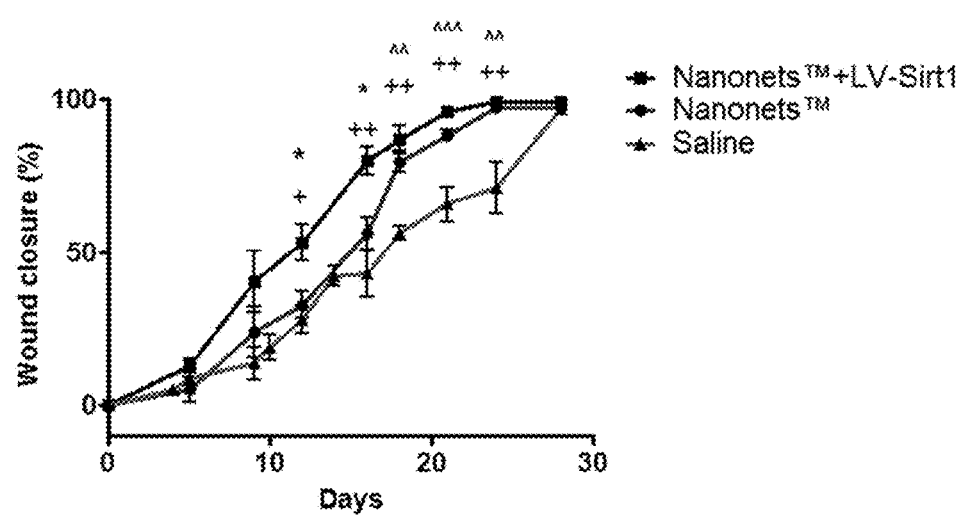

To deliver lentiviral vectors, an antioxidant/thermo-responsive dressing, PPCN, was used as a vehicle to entrap and deliver active lentiviruses. Lentiviral vectors released up to three days from PPCN can transduce human dermal fibroblasts. When injected subcutaneously in rats, lentiviruses entrapped in PPCN resulted in localized and sustained transgene expression that persisted for at least 6 weeks. PPCN has intrinsic antioxidant properties that can scavenge free radicals, chelate metal ions, inhibit lipid peroxidation. [20; herein incorporated by reference in its entirety] Wound coverage with PPCN dressing accelerated wound healing compared to saline-treated wounds (FIG. 7). As high-levels of oxidative stress impair wound healing, PPCN can attenuate the local oxidative stress and facilitate wound repair.[3; herein incorporated by reference in its entirety] Furthermore, the thermoreversible property of PPCN allow it to easily conform to the shape of the wounds and removed from the wound bed via room temperature saline rinses during dressing changes with minimal discomfort to the patient and maximum preservation of newly formed tissue.

Several studies suggest that senescence plays a role in delayed healing.[5, 32; herein incorporated by reference in its entirety] Diabetic dermal fibroblasts displaying senescence-like characteristics with reduced expression of anti-oxidant genes was linked to impaired wound healing in diabetes.[4; herein incorporated by reference in its entirety] Sirt1 is a regulator of cellular senescence through multiple mechanisms including the modulation of p53 and forkhead box O transcription factors.[10, 33, 34: herein incorporated by reference in their entireties] As aging or senescence negatively impacts wound healing, experiments were conducted during development of embodiments herein to determine whether Sirt1 overexpression prevents senescence in HDFs. Indeed, Sirt1 overexpression attenuated senescence-associated β-galactosidase activity, a reliable marker that has been widely used to study senescence.[33, 35-38; herein incorporated by reference in their entireties] Brain-specific Sirt1-overexpression transgenic mice displayed significant extension of lifespan and exhibit phenotypic signs of delayed aging.[39; herein incorporated by reference in its entirety]

Sirt1-overexpression delivered from PPCN not only accelerated wound healing, but we decreased dermal fibrosis and sped regeneration of pilosebaceous units. Inflammation was also decreased upon closure with PPCN+LV-Sirt1 treatment.

Experiments conducted during development of embodiments herein demonstrate that the Sirt1 expression and Sirt lysine deacetylase activity are significantly reduced in the skin of diabetic mice compared to healthy mice. Using an antioxidant, thermoresponsive dressing referred to as PPCN, active lentiviruses were entrapped and delivered, and allowed for localized and sustained transgene expression. LV-Sirt1 is effective at transducing human epithelial keratinocytes and dermal fibroblasts and can prevent senescence in dermal fibroblasts. Augmenting the Sirt1 expression level at the diabetic wound bed using LV-Sirt1 delivered from PPCN can accelerate and improve diabetes-impaired wound healing. Data indicates that Sirt1 and PPCN provide a therapeutic dressing to enhance healing in diabetic ulcers.

Experimental

Example 1

Sirt1 Expression and Deacetylase Activity in Dermal Tissue

Dermal tissue from male Lepr$^{db}$ mice and c57bl/6J mice of age 9-12 weeks old were homogenized in buffer D (20 mM HEPES pH 7.9, 20% glycerol, 0.1 M KCl, 0.2 mM EDTA, 0.5 mM DTT, and 0.1 mM PMSF) using a dounce tissue homogenizer. Total protein was quantified using BCA assay kit (Pierce Thermo Scientific, Rockford, Ill.). For immunoblotting, cellular proteins were fractionated using Bolt® 4-12% Bis-Tris gel (Life Technologies, Carlsbad, Calif.), electro-transferred onto a nitrocellulose membrane, and probed using anti-Sirt1 (#9475, Cell Signaling, Danvers, Mass.) and anti-β actin antibodies (#4970, Cell Signaling, Danvers, Mass.), followed by a secondary anti-rabbit IgG HRP antibody (#7074P2, Cell Signaling, Danvers, Mass.). Proteins were detected using Immobilon Chemiluminescent Substrate (EMD Millipore, Billerica, Mass.) and PXi blot imaging system (Syngene, Frederick, Md.). To measure deactylase activity, a method referred to as self-assembled monolayer desorption ionization (SAMDI) mass spectrometry was employed.[21, 22] Briefly, tissue lysates were diluted to 1.1 mg/mL protein concentration and were incubated at 37° C. for 3 hr or 16 hr with nicotinamide adenine dinucleotide, trichostatin A, and Ac-GRK$^{Ac}$HYC-NH$_2$ peptides at a final concentration of 1 mM, 50 µM, and 17.4 µM. The reaction mixtures were then quenched with 50 mM nicotinamide and transferred to a 384-gold spotted array plate with maleimide-terminated self-assembled monolayers for peptide immobilization. The plates were subsequently washed with deionized water and ethanol, dried using nitrogen, and treated with matrix (2,4,6-trihydroxyacetophenone, 20 mg/mL in acetone) and analyzed using MALDI-TOF MS. Lysine deacetylase activities were calculated from each spectrum based on the percentage conversion as previous described.[22; herein incorporated by reference in its entirety]

Production of LV-Luc and LV-GFP

Lentiviruses encoding for luciferase (LV-Luc) were provided as a gift from Prof Lonnie Shea's lab. LV-Luc was produced according to previously established techniques in which lentiviral packaging vectors, pMD2.g, pRSV-Rev, and pIVS-VSV-G, and luciferase-firefly-cloned pCS-CG (Addgene, Cambridge, Mass.) were cotransfected into HEK-293T cells using Lipofectamine 2000 (Life Technologies, Carlsbad, Calif.). The cell culture was maintained in DMEM plus 10% FBS at 37° C. and 5% CO$_2$. After 48 h of transfection, the supernatant was collected and centrifuged to pellet any residual cells. The supernatant was then concentrated using PEG-it (System Biosciences, Mountain View, Calif.), and precipitated lentiviruses were resuspended in sterile phosphate-buffered saline (PBS, pH 7.4). Lentiviruses were stored in single-use aliquots in sterile PBS at −80° C. and used within 6 months of production.

Lentiviruses encoding for GFP (LV-GFP) were produced according to previously established techniques in which lentiviral packaging vectors, pMD2.g and psPAX2, were co-transfected with pWPI (Addgene, Cambridge, Mass.) into HEK-293FT cells using Fugene HD at 3:1 total DNA mass to Fugene HD (Promega, Madison, Wis.) volume ratio complexed in Opti-MEM (Life Technologies, Carlsbad, Calif.). After 48 h of transfection, the supernatant was collected and purified using Lenti-X Maxi Purification Kit (ClonTech, Mountain View, Calif.), subsequently concentrated using Lenti-X concentrator (ClonTech, Mountain View, Calif.), and resuspended in sterile PBS. The lentivirus titer was determined using a qPCR lentivirus titration kit (Applied Biological Materials, Richmond, BC, Canada). Lentiviruses were stored in single-use aliquots in sterile PBS at −80° C. and used within 6 months of production.

PPCN Synthesis and Characterization of Lentivirus Entrapment and Release

PPCN (poly(polyethyleneglycol citrate co N-isopropylacrylamide) (PPCN)) was synthesized.[20; herein incorporated by reference in its entirety] First, citric acid, polyethylene (PEG), and glycerol 1,3-diglycerolate diacrylate in a 5:9:1 molar ratio was reacted in a polycondensation reaction at 140° C. for 45 minutes by melting under constant stirring to produce poly(polyethyleneglycol citrate) acrylate prepolymer (PPCac). Second, for free radical polymerization, PPCac and N-isopropylacrylamide (NIPAAm) were added to a three-necked flask in a 1:1 weight to weight ratio and dissolved in 1,4-dioxane. AIBN radical initiator was added to the PPCac and NIPAAm mixture (final concentration: $6.5 \times 10^{-3}$ M) and reacted for 8 hours at 65° C. in a nitrogen atmosphere. The resulting PPCN copolymer was dissolved in 1,4-dioxane and purified by precipitation in diethyl ether and vacuum dried. PPCN were gas sterilized using ethylene oxide.

Lentiviruses ($2 \times 10^8$ particles) were suspended in phosphate buffered saline (PBS) and mixed with sterile PPCN pre-dissolved in PBS (pH 7.4, 100 mg/mL). A volume of 50 uL of the PPCN solution containing lentivirus was dispensed into each well of a 96-well plate. The plate was placed in a 37° C. incubator for 30 mins for gelation. Gels were subsequently incubated in DMEM plus 10% FBS at 37° C. and 5% CO$_2$ to quantify the amount of lentiviruses released. At different time points, the medium was removed (supernatant), stored at −80° C., and fresh medium was added to the well. The amount of lentivirus released was determined by a qPCR lentivirus titration kit (Applied Biological Materials, Richmond, BC, Canada). To assess activity of released lentiviruses, lentiviruses encoding for GFP (LV-GFP) were mixed with dissolved sterile PPCN (100 mg/mL, pH 7.4 in PBS). Media was collected daily and added to HDFs cultured on tissue culture plastic. After three days of transduction, HDFs were imaged for GFP expression using a fluorescence microscope (TE2000, NIKON), and HUVECs were lysed with reporter lysis buffer (Promega, Madison, Wis.) and assessed for enzymatic activity using Luciferase Assay Reagent (Promega, Madison, Wis.). A Synergy Microplate Reader (Biotek, Winooski, Vt.) was used to calculate the relative light units (RLU), which were normalized to the total protein in the cell extract as measured using a BCA assay kit (Pierce, Rockford, Ill.).

In vivo gene expression following subcutaneous injection of lentivirus-loaded PPCN (100 µL/injection site) was determined through bioluminescence imaging. PPCN at a concentration of 125 mg/mL was diluted to 100 mg/mL using either 20 µL of lentiviruses encoding for luciferase (LV-Luc, $1\times10^6$ particles/µL) or 20 µL of PBS. Under deep isoflurane-$O_2$ general anesthesia, each rat received four subcutaneous injections randomly assigned to receive PPCN+LV-Luc or PPCN. Before imaging, animals were anesthetized and received an intraperitoneal injection of 150 mg/kg of body weight of D-luciferin (Biovision, Milpitas, Calif.). Animals were monitored over time for transgene expression using IVIS imaging system (Caliper Life Sciences, Hopkinton, Mass.). Constant-size regions of interest over the implant site were used for radiance quantification (photons per second per centimeter square per steradian). Animals were cared for in compliance with the regulations established by the Northwestern University Institutional Animal Care and Use Committee.

Production of LV-Sirt1 and LV-Sirt1 Mutant

Sirt1 and Sirt1 mutant (Addgene plasmid 1791 and 1792, respectively) were cloned into a modified lentiviral transfer vector, pWPI, such that sequence encoding for EGFP was removed using BmgBI and BstBI digestions. Lentiviral packaging vectors, pMD2.g and psPAX2, were co-transfected with pWPI, pWPI-Sirt1, or pWPI-Sirt1 mutant (H363Y) (mass ratio 1:3:4, respectively) into HEK-293FT cells using Fugene HD at 3:1 total DNA mass to Fugene HD (Promega, Madison, Wis.) volume ratio complexed in Opti-MEM (Life Technologies, Carlsbad, Calif.). After 48 h of transfection, the supernatant was collected and purified using Lenti-X Maxi Purification Kit (ClonTech, Mountain View, Calif.) and subsequently concentrated using Lenti-X concentrator (ClonTech, Mountain View, Calif.). The lentivirus titer was determined using a qPCR lentivirus titration kit (Applied Biological Materials, Richmond, BC, Canada).

Transduction and Characterization of Human Epithelial Keratinocytes and Human Dermal Fibroblasts Human epithelial keratinocytes (HEKs, Lonza, Walkersville, Md.) and human dermal fibroblasts (HDFs) were transduced with empty vector lentiviruses or lentiviruses encoding for Sirt1 or Sirt1 mutant. For immunoblotting, cellular proteins were extracted using radioimmunoprecipitation assay buffer (RIPA). Proteins were fractionated using Bolt® 4-12% Bis-Tris gel (Life Technologies, Carlsbad, Calif.), electro-transferred onto a nitrocellulose membrane, and probed using anti-Sirt1 (#9475, Cell Signaling, Danvers, Mass.) and anti-β actin antibodies (#4970, Cell Signaling, Danvers, Mass.), followed by a secondary anti-rabbit IgG HRP antibody (#7074P2, Cell Signaling, Danvers, Mass.). Proteins were detected using Immobilon Chemiluminescent Substrate (EMD Millipore, Billerica, Mass.) and PXi blot imaging system (Syngene, Frederick, Md.). For immunofluorescence, HEKs and HDFs were fixed with cold methanol and incubated with anti-Sirt1 primary antibody (sc-15404, Santa Cruz Biotechnology, Dallas, Tex.), followed by a secondary goat anti-rabbit fluorescent antibody (Life Technologies, Carlsbad, Calif.). Nuclei were stained with Hoescht 33342 (Sigma, St Louis, Mo.) and cells were imaged using a fluorescence microscope (TE2000, NIKON).

Figure 8:
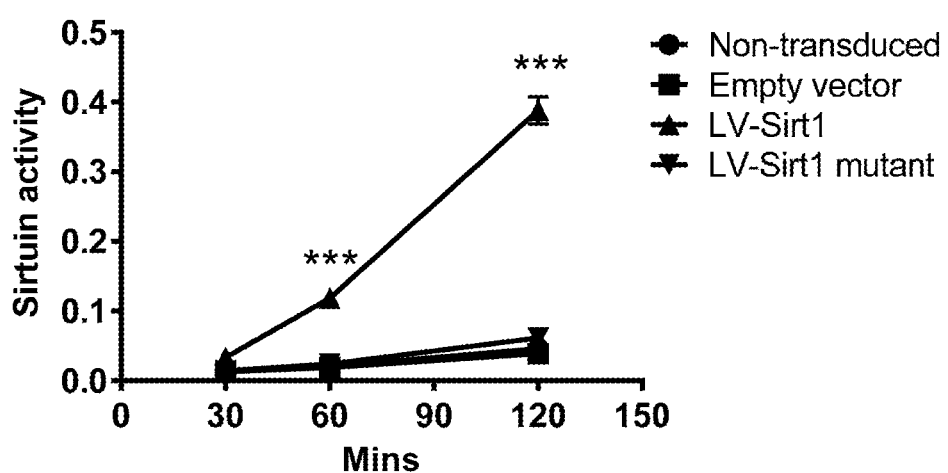
FIG. 8. Sirtuin activity from cell lysates measured using self-assembled monolayer desorption ionization (SAMDI) technique. Sirt1-overexpressing cells have significantly higher lysine deacetylase activity with increasing incubation time suggesting greater enzymatic activity. Conversely, non-, empty vector, and Sirt1-mutant transduced cells have modest increase in deacetylase activity.

The increased sirtuin deacetylase activity in the transduced cells was confirmed using SAMDI (FIG. 8).

Senescence Associated β-Galactosidase Assay

HDFs transduced at passages 3-5 were allowed to age to passages>10. Cells were lysed using a cellular senescence assay kit (Cell BioLabs, San Diego, Calif.) following manufacturer's protocol. The activity of β-galactosidase was quantified using a fluorescence plate reader (Molecular Dynamics M3, Sunnyvale, Calif.).

Full-Thickness Excisional Dorsal Skin Wounds and Application of the PPCN

Two dorsal splinted excisional wounds were created in 8-10 weeks old male Lepr$^{db}$ mice (Jackson Laboratory, Bar Harbor, Me.) as previously described by Galiano et al.[23; herein incorporated by reference in its entirety]. Mice were anesthetized and dorsal fur was removed by shaving with an electric clipper followed by application of a depilatory cream. The skin was sterilized by alternating applications of betadine and alcohol swabs. Mice were subcutaneously injected with buprenorphine (0.5 mg/kg). A 6 mm punch biopsy (Acuderm, Fort Lauderdale, Fla.) was marked with a surgical marker and was used to gently outline two wounds on each side of the mouse's midline. Following the outline, full-thickness wounds were made using a McPherson-Vannas Micro Scissor (World Precision Instruments, Sarasota, Fla.). Each mouse received two ethylene oxide gas-sterilized, donut-shaped splints that were positioned such that the wounds were centered within the splint. The splints (OD 16 mm, ID 10 mm) were fabricated from a 1 mm-thick acrylic tape (3M, Saint Paul, Minn.). Tissue adhesive (Vetbond, 3M, Saint Paul, Minn.) and interrupted 6-0 nylon sutures were used to fix the splint to the skin. Each of the two wounds was randomly assigned to receive either 40 uL of sterile PPCN (100 mg/mL, pH 7.4 in PBS) or PPCN+LV-Sirt1 (100 mg/mL, pH 7.4 in PBS; $2\times10^7$ particles). In a separate experiment, wounds were also randomly assigned to receive either 40 uL of sterile saline (pH 7.4, PBS) or LV-Sirt1 ($2\times10^7$ particles, pH 7.4 in PBS). After the material gels and application of treatment, an occlusive film (Tegaderm, 3M, Saint Paul, Minn.) was used to cover the wounds and the animals were placed singly caged and allowed to recover from isoflurane anesthesia. PPCN (100 mg/mL, pH 7.4 in PBS) or PPCN+LV-Sirt1 (100 mg/mL, pH 7.4 in PBS; $2\times10^7$ particles) was reapplied 5 days after initial wounding. Animals were cared for in compliance with the regulations established by the Northwestern University Institutional Animal Care and Use Committee.

Wound Analysis

Digital photographs were taken on the day of the surgery and every 2-4 days thereafter. Wound area was analyzed by tracing the wound margin and calculating pixel area using ImageJ software (National Institutes of Health). The wound area at each time point was normalized to the fixed inner area of the splint. The wound closure rate was calculated by the following formula:

$$\% \text{ wound closure} = 100 * \left( 1 - \frac{\left(\frac{\text{Day } X \text{ wound area}}{\text{Day } X \text{ splint area}}\right)}{\frac{\text{Day 0 wound area}}{\text{Day 0 splint area}}} \right)$$

Figure 9:
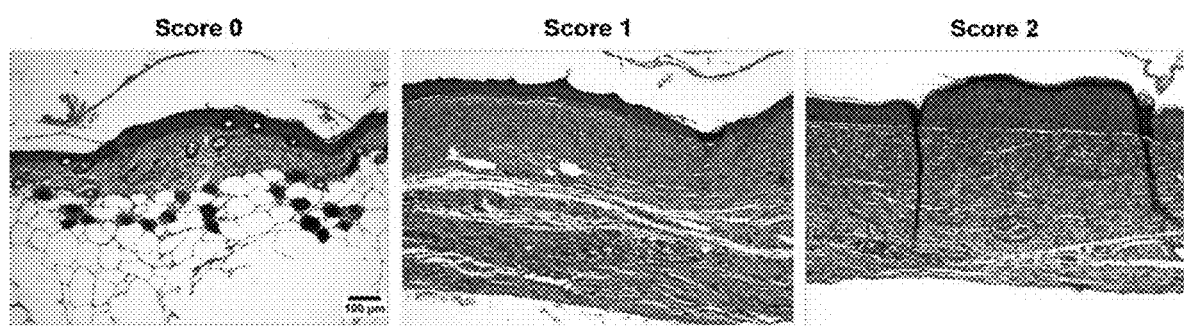
FIG. 9. Representative histological H&E images of inflammatory score of 0 (left; very few, scattered round dark lymphocytes), score of 1 (middle; mixed population of more lymphocytes and histiocytes), and score of 2 (right; aggregates of lymphocytes and histiocytes in deeper dermis and many scattered cells in upper dermis).

After complete wound closure, approximately 24 days post-surgery, regenerated dermal tissue was excised and fixed in paraformaldehyde (4%). Tissue samples were embedded in paraffin, sectioned, and underwent routine histological processing with hematoxylin and eosin (H&E). Dermal fibrosis was quantified using ImageJ (NIH, Bethesda, Md.) and pilosebaceous units were also blindly quantified from H&E images. Images were semi-quantitatively scored (0=none to very minimal, 1=scant, 2=moderate, and 3=abundant) by a blinded dermatopathologist for the extent of angiogenesis and inflammation (FIG. 9). For immunohistochemistry, sections were deparaffinized, rehydrated, and underwent antigen retrieval using a sodium citrate buffer. Sections incubated with an anti-involucrin primary antibody (sc-28558 Santa Cruz Biotechnology, Dallas, Tex.) were stained by a secondary goat anti-rabbit fluorescent antibody (Life Technologies, Carlsbad, Calif.). Sections incubated with an anti-Sirt1 antibody (sc-15404, Santa Cruz Biotechnology, Dallas, Tex.) were subsequently incubated with a biotinylated secondary antibody from the Histo SP IHC Kit, (Life Technologies, #95-9643), followed by streptavidin-HRP. Color was developed with DAB and $H_2O_2$, and sections were dehydrated and mounted in cryostat medium.

Statistical Analysis

Results are expressed as mean±SEM. Statistical analysis was conducted using GraphPad Prism software (La Jolla, Calif.). Statistical significance between two groups was compared using unpaired Student t tests. For three or more groups, statistical significance was compared using a one-way ANOVA followed by Tukey posthoc test. A level of $p \leq 0.05$ was accepted as significant.

Example 2

Results

Sirt1 Expression and Deacetylase Activity are Decreased in the Skin of Diabetic Mice Experiments were conducted during development of embodiments herein to probe the expression of Sirt1 in the skin of diabetic mice compared to healthy control mice of the same background strain. Immunoblot analyses revealed that the Sirt1 expression is significantly lower in the skin of diabetic mice when compared to healthy control mice (FIG. 1A). Using self-assembled monolayer desorption ionization (SAMDI) mass spectrometry assay, sirtuin deacetylase activity was measured from skin tissue lysates. Similar to the decrease in Sirt1 expression in diabetic mice skin, the sirtuin deacetylase activity as per the SAMDI data is lower in diabetic mice skin samples compared to healthy control mice (FIG. 1B).

PPCN is Effective at Entrapping and Slowly Releasing Active Lentiviruses

PPCN, a biodegradable antioxidant and thermoresponsive hydrogel, is an effective vehicle to deliver lentiviruses for localized and sustained transgene expression. PPCN™ in the liquid form was mixed with lentiviruses that encode for GFP (LV-GFP) or luciferase (LV-Luc) and subsequently gelled at 37° C. Approximately 50% of lentiviruses were released in the first day (FIG. 2A). Lentiviral vectors were continually released for up to three days. Furthermore, the released lentiviruses were bioactive and transduced HDFs and HUVECs (FIG. 2B). Releasates from day 1 resulted in the greatest number of cells positive for GFP and greatest luciferase transgene expression. No released lentiviruses or transgene expression was observed after three days. These results confirm that PPCN™ can release active lentivirus particles entrapped in the polymer network and preserve their infectivity.

Lentivirus encoding for luciferase (LV-Luc) were successfully entrapped in PPCN and formed a gel in situ upon subcutaneous injection. Based on the bioluminescence imaging data, transgene expression persisted for at least 6 weeks and was statistically significant compared to PPCN without lentivirus at all time points (FIG. 2C). The transgene expression peaked at 2 weeks and decreased gradually over time.

HEKa and HDF Overexpress Sirt1 and Sirt1 Mutant

To evaluate sustained and localized transgene expression in vivo, lentivirus encoding for Sirt1 and Sirt1 mutant (LV-Sirt1 and LV-Sirt1 mutant) were constructed and transduced HEKa and HDF. Both HEKa and HDF when transduced overexpress the desired transgene (FIG. 5-3). From the immunofluorescence images, Sirt1 overexpression is predominantly localized to the nucleus which is consistent with reports in the literature.[24]

Sirt1 Overexpression Prevents HDF Senescence

Figure 4:
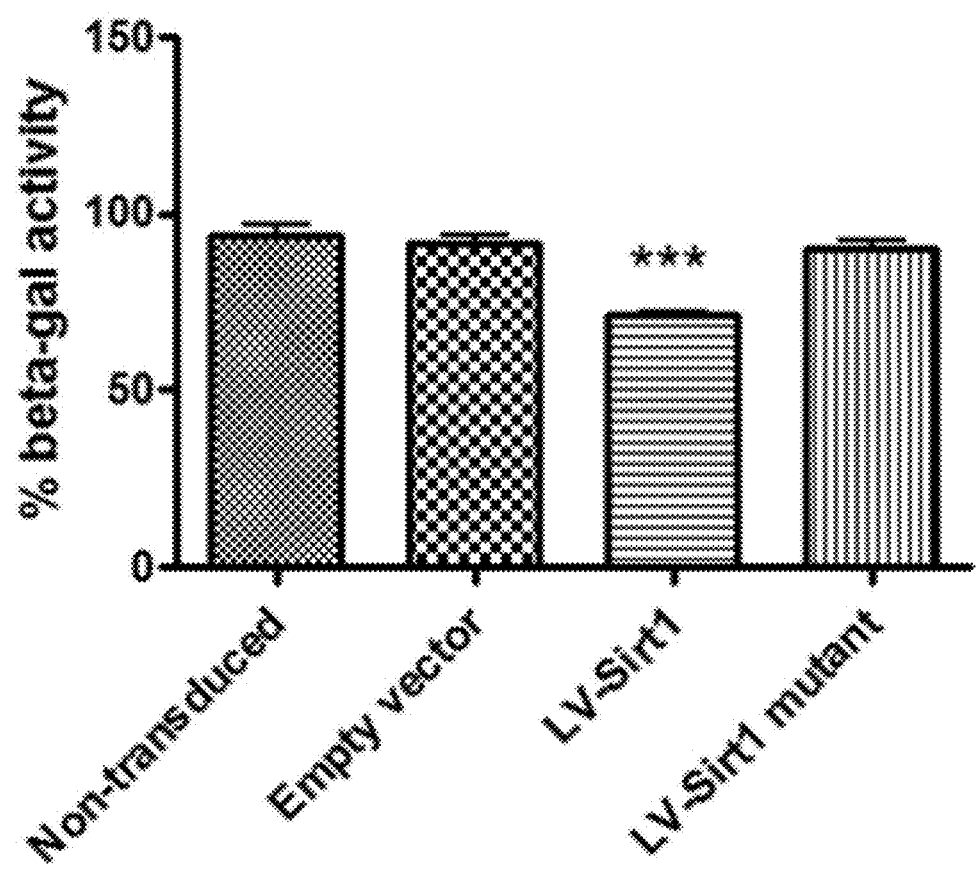
FIG. 4. Sirt1 overexpression inhibits HDF senescence. HDF transduced with LV-Sirt1 have significantly less β-galactosidase activity compared to non-, empty vector-, and LV-Sirt1 mutant-transduced groups (n=4, Mean±SEM).

Results indicate that Sirt1 overexpression can attenuate replicative-induced HDF senescence. Compared to control groups, Sirt1-overexpressing HDFs have approximately 30% less β-galactosidase activity (FIG. 4).

Sirt1 Overexpression at the Wound Bed Accelerates Diabetes-Impaired Wound Healing To assess whether augmenting the Sirt1 expression in the wound bed of diabetic mice will improve diabetes-impaired wound healing, we generated two full-thickness, 6 mm-diameter circular wounds on each side of the diabetic mice midline. Wounds were randomly assigned to receive either saline, PPCN™, or PPCN+LV-Sirt1 treatment.

Figure 5A:
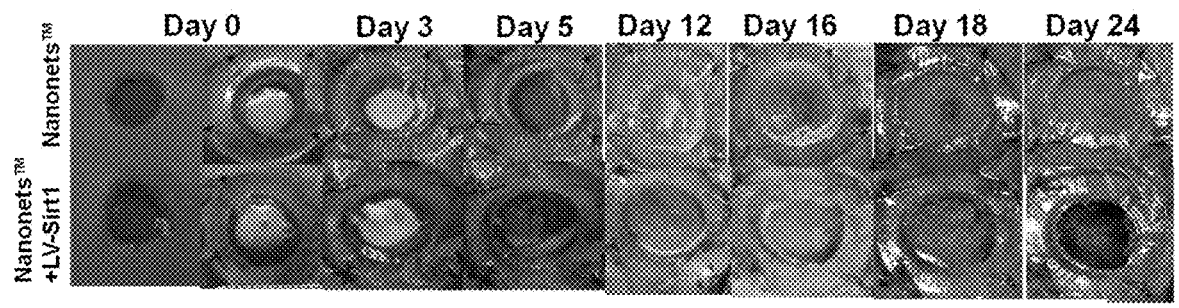
FIGS. 5A-C. Sirt1 overexpression accelerates diabetes-impaired wound healing. A: PPCN or PPCN+LV-Sirt1 treatments were randomly assigned to each full-thickness wound centered within sutured donut-shaped splits. Wound closure rates were expressed as a percentage of the closed wound area. Wounds treated with PPCN+LV-Sirt1 have accelerated wound closure compared to PPCN-treated wounds (n≥6, Mean±SEM, *p<0.05). B: Matched-control wounds of faster regeneration of pilosebaceous units for PPCN+LV-Sirt1-treated wounds at day 21. C: Saline or LV-Sirt1 treatments were randomly assigned to each full-thickness wound centered within sutured donut-shaped splits. Wound closure rates were expressed as a percentage of the closed wound area. Wounds treated with LV-Sirt1 have accelerated wound closure compared to PPCN-treated wounds (n≥3, Mean±SEM, *p<0.05).
Figure 5A:
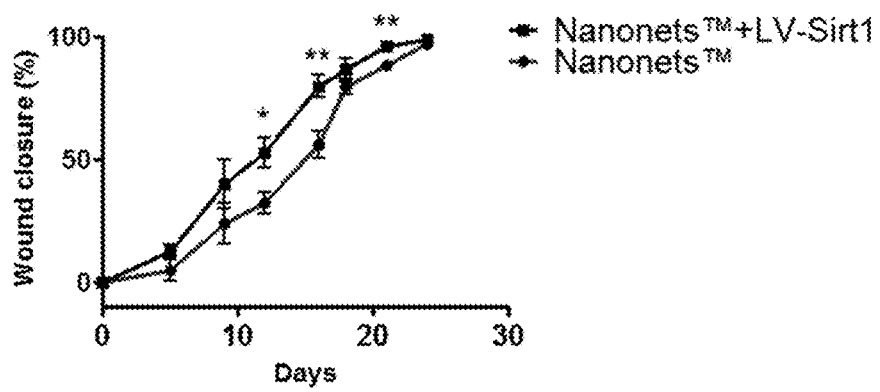
Figure 5B:
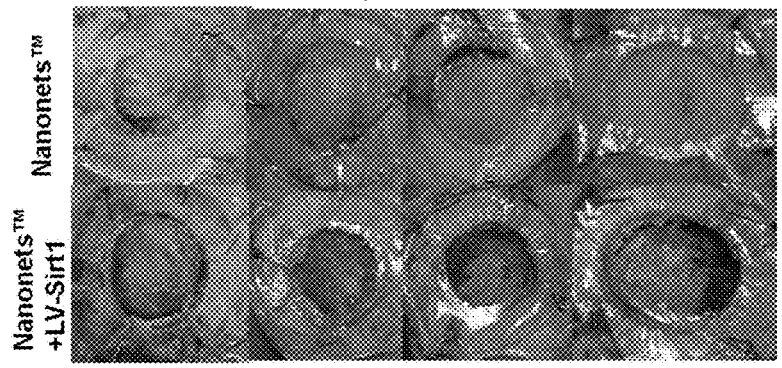
Figure 5C:
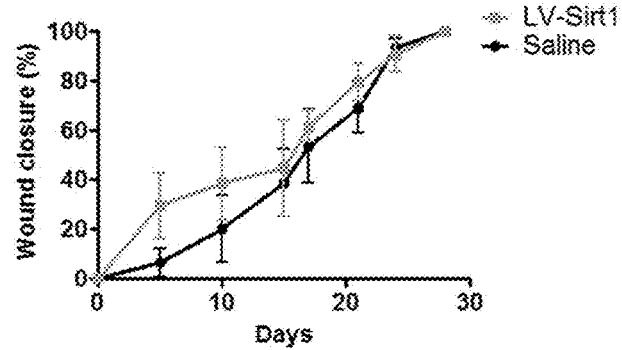

Wounds treated with PPCN+LV-Sirt1 closed at a faster rate compared to matched control PPCN-treated wounds (FIG. 5A). Wound closure % for PPCN+LV-Sirt1 was significantly higher than PPCN at days 12 and 16. PPCN™+ LV-Sirt1 and PPCN™ treatments also significantly increased wound closure compared to saline treatment at days 18, 21, and 24. Gross digital images demonstrate that PPCN+LV-Sirt1-treated wounds exhibited faster regeneration of pilosebaceous units at day 21 (FIG. 5B). Wounds treated with LV-Sirt1 suspended in saline also improved wound closure rate compared to matched control saline-treated wounds (FIG. 5C).

Sirt1 Overexpression at the Wound Bed Reduces Dermal Fibrosis

Figure 6A:
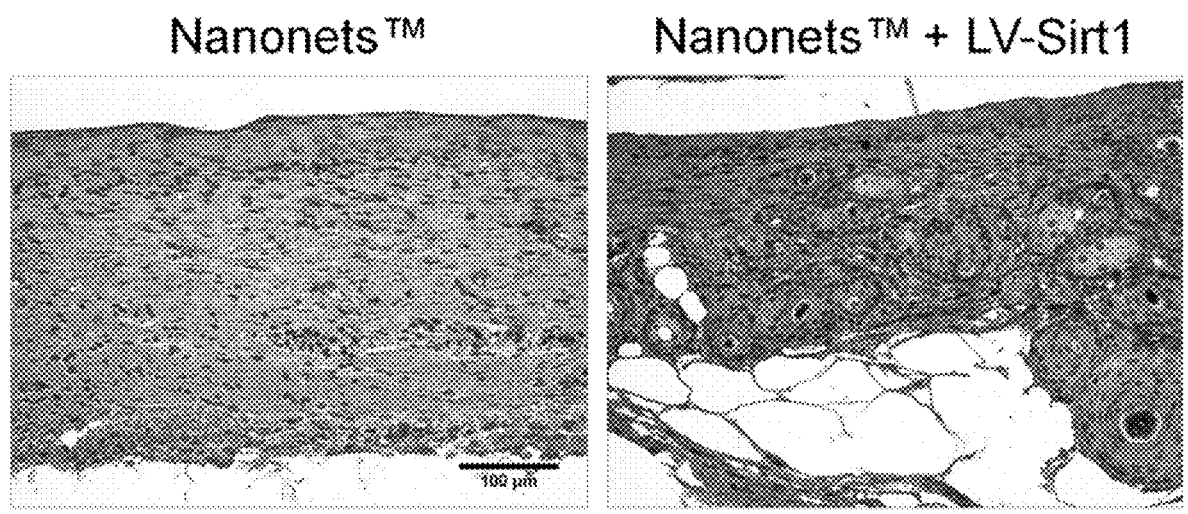
FIGS. 6A-6B. PPCN+LV-Sirt1-treated wounds have moderately less fibrosis, inflammation, and vascularization. A: Immunohistochemistry for Sirt1 (brown) of regenerated dermal tissue after wound closure demonstrating higher Sirt1 expression, less dermal fibrosis, and faster regeneration of pilosebaceous units. B: Hematoxylin and eosin stains of the regenerated tissue at wound closure. Dermal fibrosis was quantified and the extent of inflammation and angiogenesis was semi-quantitatively scored by a blinded expert dermatopathologist (n=5, Mean±SEM).
Figure 6B:
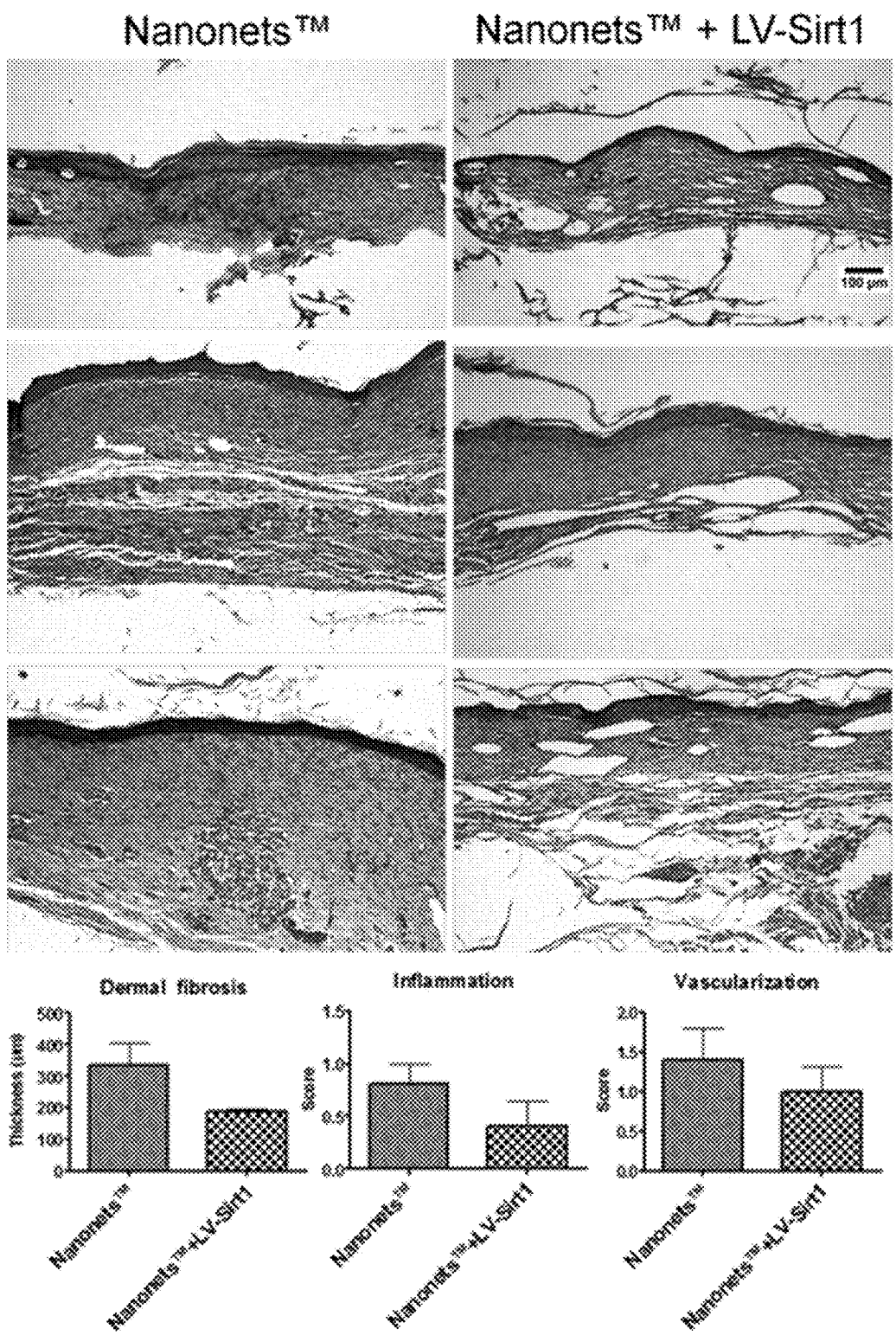

After wound closure (24 days post-wounding), the regenerated dermal tissues were excised and stained for histologic evaluation. Immunohistochemistry for Sirt1 demonstrated higher Sirt1 expression in the regenerated tissue. (FIG. 6A) Although not statistically significant, PPCN+LV-Sirt1-treatment moderately decreases fibrosis, inflammation, and vascularization compared to PPCN only treatment (FIG. 6B).

REFERENCES

The following references are herein incorporated by reference in their entireties.

[1] Galiano R D, Tepper O M, Pelo C R, Bhatt K A, Callaghan M, Bastidas N, et al. Topical Vascular Endothelial Growth Factor Accelerates Diabetic Wound Healing through Increased Angiogenesis and by Mobilizing and Recruiting Bone Marrow-Derived Cells. The American Journal of Pathology. 2004; 164:1935-47.

[2] Eming S A, Krieg T, Davidson J M. Inflammation in Wound Repair: Molecular and Cellular Mechanisms. J Invest Dermatol. 2007; 127:514-25.

[3] Schafer M, Werner S. Oxidative stress in normal and impaired wound repair. Pharmacological Research. 2008; 58:165-71.

[4] Bitar M S, Abdel-Halim S M, Al-Mulla F. Caveolin-1/PTRF upregulation constitutes a mechanism for mediating p53-induced cellular senescence: implications for evidence-based therapy of delayed wound healing in diabetes. Am J Physiol Endocrinol Metab. 2013; 305: E951-E63.

[5] Telgenhoff D, Shroot B. Cellular senescence mechanisms in chronic wound healing. Cell Death Differ. 2005; 12:695-8.

[6] Yuen D A Z Y, Thai K, Spring C, Chan L, Guo X, Advani A, Sivak J M, Gilbert R E. Angiogenic Dysfunction in Bone Marrow-Derived Early Outgrowth Cells from Diabetic Animals Is Attenuated by SIRT1 Activation. Stem cells translational medicine. 2012; 1:921-6.

[7] Potente M, Ghaeni L, Baldessari D, Mostoslaysky R, Rossig L, Dequiedt F, et al. SIRT1 controls endothelial angiogenic functions during vascular growth. Genes & Development. 2007; 21:2644-58.

[8] Yeung F, Hoberg J E, Ramsey C S, Keller M D, Jones D R, Frye R A, et al. Modulation of NF-[kappa]B-dependent transcription and cell survival by the SIRT1 deacetylase. EMBO J. 2004; 23:2369-80.

[9] Brunet A, Sweeney L B, Sturgill J F, Chua K F, Greer P L, Lin Y, et al. Stress-Dependent Regulation of FOXO Transcription Factors by the SIRT1 Deacetylase. Science. 2004; 303:2011-5.

[10] Langley E, Pearson M, Faretta M, Bauer U-M, Frye R A, Minucci S, et al. Human SIR2 deacetylates p53 and antagonizes PML/p53-induced cellular senescence. The EMBO Journal. 2002; 21:2383-96.

[11] Blander G, Bhimavarapu A, Mammone T, Maes D, Elliston K, Reich C, et al. SIRT1 Promotes Differentiation of Normal Human Keratinocytes. J Invest Dermatol. 2008; 129:41-9.

[12] Ming M, Shea C R, Guo X, Li X, Soltani K, Han W, et al. Regulation of global genome nucleotide excision repair by SIRT1 through xeroderma pigmentosum C. Proceedings of the National Academy of Sciences. 2010; 107:22623-8.

[13] Fan W, Luo J. SIRT1 Regulates UV-Induced DNA Repair through Deacetylating XPA. Molecular Cell. 2010; 39:247-58.

[14] Sun C, Zhang F, Ge X, Yan T, Chen X, Shi X, et al. SIRT1 Improves Insulin Sensitivity under Insulin-Resistant Conditions by Repressing PTP1B. Cell Metabolism. 2007; 6:307-19.

[15] Hasegawa K, Wakino S, Simic P, Sakamaki Y, Minakuchi H, Fujimura K, et al. Renal tubular Sirt1 attenuates diabetic albuminuria by epigenetically suppressing Claudin-1 overexpression in podocytes. Nat Med. 2013; 19:1496-504.

[16] Rodgers J, Lerin C, Haas W, Gygi S, Spiegelman B, Puigserver P. Nutrient control of glucose homeostasis through a complex of PGC-1alpha and SIRT1. Nature. 2005; 434:113-8.

[17] Banks A S, Kon N, Knight C, Matsumoto M, Gutierrez-Juarez R, Rossetti L, et al. SirT1 Gain of Function Increases Energy Efficiency and Prevents Diabetes in Mice. Cell Metabolism. 2008; 8:333-41.

[18] Orimo M, Minamino T, Miyauchi H, Tateno K, Okada S, Moriya J, et al. Protective Role of SIRT1 in Diabetic Vascular Dysfunction. Arteriosclerosis, Thrombosis, and Vascular Biology. 2009; 29:889-94.

[19] Toniolo A, Warden E A, Nassi A, Cignarella A, Bolego C. Regulation of SIRT1 in Vascular Smooth Muscle Cells from Streptozotocin-Diabetic Rats. PLoS ONE. 2013; 8:e65666.

[20] Yang J, van Lith R, Baler K, Hoshi R A, Ameer G A. A Thermoresponsive Biodegradable Polymer with Intrinsic Antioxidant Properties. Biomacromolecules. 2014.

[21] Kuo H-Y, DeLuca T A, Miller W M, Mrksich M. Profiling Deacetylase Activities in Cell Lysates with Peptide Arrays and SAMDI Mass Spectrometry. Analytical Chemistry. 2013; 85:10635-42.

[22] Gurard-Levin Z A, Kilian K A, Kim J, Bahr K, Mrksich M. Peptide Arrays Identify Isoform-Selective Substrates for Profiling Endogenous Lysine Deacetylase Activity. ACS Chemical Biology. 2010; 5:863-73.

[23] Galiano R D, Michaels V J, Dobryansky M, Levine J P, Gurtner G C. Quantitative and reproducible murine model of excisional wound healing. Wound Repair and Regeneration. 2004; 12:485-92.

[24] Michishita E, Park J Y, Burneskis J M, Barrett J C, Horikawa I. Evolutionarily Conserved and Nonconserved Cellular Localizations and Functions of Human SIRT Proteins. Molecular Biology of the Cell. 2005; 16:4623-35.

[25] Kaeberlein M, McDonagh T, Heltweg B, Hixon J, Westman E A, Caldwell S D, et al. Substrate-specific Activation of Sirtuins by Resveratrol. Journal of Biological Chemistry. 2005; 280:17038-45.

[26] Su J, Rajapaksha T W, Peter M E, Mrksich M. Assays of Endogenous Caspase Activities: A Comparison of Mass Spectrometry and Fluorescence Formats. Analytical Chemistry. 2006; 78:4945-51.

[27] Gillum M P, Kotas M E, Erion D M, Kursawe R, Chatterjee P, Nead K T, et al. SirT1 Regulates Adipose Tissue Inflammation. Diabetes. 2011; 60:3235-45.

[28] Lee J-H, Song M-Y, Song E-K, Kim E-K, Moon W S, Han M-K, et al. Overexpression of SIRT1 Protects Pancreatic β-Cells Against Cytokine Toxicity by Suppressing the Nuclear Factor-κB Signaling Pathway. Diabetes. 2009; 58:344-51.

[29] Yang Z, Kahn B B, Shi H, Xue B-z. Macrophage α1 AMP-activated Protein Kinase (α1AMPK) Antagonizes Fatty Acid-induced Inflammation through SIRT1. Journal of Biological Chemistry. 2010; 285:19051-9.

[30] Branski L K, Pereira C T, Herndon D N, Jeschke M G. Gene therapy in wound healing: present status and future directions. Gene Ther. 2006; 14:1-10.

[31] Papanas D, Maltezos E. Benefit-Risk Assessment of Becaplermin in the Treatment of Diabetic Foot Ulcers. Drug-Safety. 2010; 33:455-61.

[32] Clark R A F. Oxidative Stress and "Senescent" Fibroblasts in Non-Healing Wounds as Potential Therapeutic Targets. J Invest Dermatol. 2008; 128:2361-4.

[33] Warboys C M, de Luca A, Amini N, Luong L, Duckles H, Hsiao S, et al. Disturbed Flow Promotes Endothelial Senescence via a p53-Dependent Pathway. Arteriosclerosis, Thrombosis, and Vascular Biology. 2014.

[34] Yao H, Chung S, Hwang J-w, Rajendrasozhan S, Sundar I K, Dean D A, et al. SIRT1 protects against emphysema via FOXO3-mediated reduction of premature senescence in mice. The Journal of Clinical Investigation. 2012; 122:2032-45.

[35] Takemura A, Iijima K, Ota H, Son B-K, Ito Y, Ogawa S, et al. Sirtuin 1 Retards Hyperphosphatemia-Induced Calcification of Vascular Smooth Muscle Cells. Arteriosclerosis, Thrombosis, and Vascular Biology. 2011; 31:2054-62.

[36] Fenton M, Barker S, Kurz D J, Erusalimsky J D. Cellular Senescence After Single and Repeated Balloon Catheter Denudations of Rabbit Carotid Arteries. Arteriosclerosis, Thrombosis, and Vascular Biology. 2001; 21:220-6.

[37] VASILE E, TOMITA Y, BROWN LF, KOCHER O, DVORAK H F. Differential expression of thymosin β-10 by early passage and senescent vascular endothelium is modulated by VPF/VEGF: evidence for senescent endothelial cells in vivo at sites of atherosclerosis. The FASEB Journal. 2001; 15:458-66.

[38] Dimri G P, Lee X, Basile G, Acosta M, Scott G, Roskelley C, et al. A biomarker that identifies senescent human cells in culture and in aging skin in vivo. Proceedings of the National Academy of Sciences. 1995; 92:9363-7.

[39] Satoh A, Brace Cynthia S, Rensing N, Cliften P, Wozniak David F, Herzog Erik D, et al. Sirt1 Extends Life Span and Delays Aging in Mice through the Regulation of Nk2 Homeobox 1 in the DMH and LH. Cell Metabolism. 2013; 18:416-30.

[40] Herranz D, Munoz-Martin M, Canamero M, Mulero F, Martinez-Pastor B, Fernandez-Capetillo O, et al. Sirt1 improves healthy ageing and protects from metabolic syndrome-associated cancer. Nat Commun. 2010; 1:3.

[41] Spallotta F, Cencioni C, Straino S, Nanni S, Rosati J, Artuso S, et al. A Nitric Oxide-dependent Crosstalk Between Class I and III Histone Deacetylases Accelerates Skin Repair. Journal of Biological Chemistry. 2013.

The invention claimed is:

1. A method of promoting wound healing in a mammalian subject comprising topically administering to the wound a composition comprising (a) an expression vector comprising a nucleic acid sequence with at least 70% sequence identity with SEQ ID NO: 1 and encoding a Sirt1 polypeptide that exhibits deacetylase activity and (b) a poly(polyethyleneglycol co-citric acid-co-N isopropylacrylamide) (PPCN) carrier material, under conditions that allow for overexpression of the Sirt1 polypeptide at the wound such that wound healing is promoted.

2. The method of claim 1, wherein the expression vector is a viral vector.

3. The method of claim 2, wherein the viral vector is a lentiviral particle.

4. The method of claim 2, wherein the viral vector is a adenovirus, Adeno-associated virus, or retrovirus.

* * * * *

SEQUENCE LISTING

<160> NUMBER OF SEQ ID NOS: 2

<210> SEQ ID NO 1
<211> LENGTH: 4110
<212> TYPE: DNA
<213> ORGANISM: Homo sapiens

<400> SEQUENCE: 1

```
gtcgagcggg agcagaggag gcgagggagg agggccagag aggcagttgg aagatggcgg      60
acgaggcggc cctcgccctt cagcccggcg gctcccccta ggcggcgggg gccgacaggg     120
aggccgcgtc gtcccccgcc ggggagccgc tccgcaagag gccgcggaga gatggtcccg     180
gcctcgagcg gagcccgggc gagcccggtg gggcggcccc agagcgtgag gtgccggcgc     240
cggccagggg ctgcccgggt gcggcggcgg cggcgctgtg gcgggaggcg gaggcagagg     300
cggcggcggc aggcggggag caagaggccc aggcgactgc ggcggctggg gaaggagaca     360
atgggccggg cctgcagggc ccatctcggg agccaccgct ggccgacaac ttgtacgacg     420
aagacgacga cgacgagggc gaggaggagg aagaggcggc ggcggcggcg attgggtacc     480
gagataacct tctgttcggt gatgaaatta tcactaatgg ttttcattcc tgtgaaagtg     540
atgaggagga tagagcctca catgcaagct ctagtgactg gactccaagg ccacggatag     600
gtccatatac ttttgttcag caacatctta tgattggcac agatcctcga acaattctta     660
aagatttatt gccggaaaca atacctccac ctgagttgga tgatatgaca ctgtggcaga     720
ttgttattaa tatcctttca gaaccaccaa aaaggaaaaa aagaaaagat attaatacaa     780
ttgaagatgc tgtgaaatta ctgcaagagt gcaaaaaaat tatagttcta actggagctg     840
gggtgtctgt ttcatgtgga atacctgact tcaggtcaag ggatggtatt tatgctcgcc     900
ttgctgtaga cttcccagat cttccagatc ctcaagcgat gtttgatatt gaatatttca     960
gaaaagatcc aagaccattc ttcaagtttg caaaggaaat atatcctgga caattccagc    1020
catctctctg tcacaaattc atagccttgt cagataagga aggaaaacta cttcgcaact    1080
atacccagaa catagacacg ctggaacagg ttgcgggaat ccaaaggata attcagtgtc    1140
atggttcctt tgcaacagca tcttgcctga tttgtaaata caaagttgac tgtgaagctg    1200
tacgaggaga tatttttaat caggtagttc ctcgatgtcc taggtgccca gctgatgaac    1260
cgcttgctat catgaaacca gagattgtgt ttttggtga aaatttacca gaacagtttc    1320
atagagccat gaagtatgac aaagatgaag ttgacctcct cattgttatt gggtcttccc    1380
tcaaagtaag accagtagca ctaattccaa gttccatacc ccatgaagtg cctcagatat    1440
taattaatag agaacctttg cctcatctgc attttgatgt agagcttctt ggagactgtg    1500
atgtcataat taatgaattg tgtcataggt taggtggtga atatgccaaa ctttgctgta    1560
```

```
accctgtaaa gctttcagaa attactgaaa aacctccacg aacacaaaaa gaattggctt    1620
atttgtcaga gttgccaccc acacctcttc atgtttcaga agactcaagt tcaccagaaa    1680
gaacttcacc accagattct tcagtgattg tcacactttt agaccaagca gctaagagta    1740
atgatgattt agatgtgtct gaatcaaaag gttgtatgga agaaaaacca caggaagtac    1800
aaacttctag gaatgttgaa agtattgctg aacagatgga aaatccggat ttgaagaatg    1860
ttggttctag tactggggag aaaaatgaaa gaacttcagt ggctggaaca gtgagaaaat    1920
gctggcctaa tagagtggca aaggagcaga ttagtaggcg gcttgatggt aatcagtatc    1980 tgttttttgcc accaaatcgt tacatttttcc atggcgctga ggtatattca gactctgaag    2040
atgacgtctt atcctctagt tcttgtggca gtaacagtga tagtgggaca tgccagagtc    2100
caagtttaga agaacccatg gaggatgaaa gtgaaattga agaattctac aatggcttag    2160
aagatgagcc tgatgttcca gagagagctg gaggagctgg atttgggact gatggagatg    2220
atcaagaggc aattaatgaa gctatatctg tgaaacagga agtaacagac atgaactatc    2280
catcaaacaa atcatagtgt aataattgtg caggtacagg aattgttcca ccagcattag    2340
gaactttagc atgtcaaaat gaatgtttac ttgtgaactc gatagagcaa ggaaaccaga    2400
aaggtgtaat atttataggt tggtaaaata gattgttttt catggataat ttttaacttc    2460
attatttctg tacttgtaca aactcaacac taactttttt tttttaaaa aaaaaaggt     2520 actaagtatc ttcaatcagc tgttggtcaa gactaacttt cttttaaagg ttcatttgta    2580
tgataaattc atatgtgtat atataatttt ttttgttttg tctagtgagt ttcaacattt    2640 ttaaagttttt caaaaagcca tcggaatgtt aaattaatgt aaagggaaca gctaatctag    2700
accaaagaat ggtattttca cttttctttg taacattgaa tggtttgaag tactcaaaat    2760
ctgttacgct aaacttttga ttcttttaaca caattatttt taaacactgg catttttccaa   2820 aactgtggca gctaactttt taaaatctca aatgacatgc agtgtgagta aaggaagtc    2880 aacaatatgt ggggagagca ctcggttgtc tttacttta aaagtaatac ttggtgctaa     2940 gaattttcagg attattgtat ttacgttcaa atgaagatgg cttttgtact tcctgtggac    3000
atgtagtaat gtctatattg gctcataaaa ctaacctgaa aaacaaataa atgctttgga    3060
aatgtttcag ttgctttaga aacattagtg cctgcctgga tccccttagt tttgaaatat    3120
ttgccattgt tgtttaaata cctatcactg tggtagagct tgcattgatc ttttccacaa    3180
gtattaaact gccaaaatgt gaatatgcaa agcctttctg aatctataat aatggtactt    3240
ctactgggga gagtgtaata ttttggactg ctgttttcca ttaatgagga gagcaacagg    3300
cccctgatta tacagttcca aagtaataag atgttaattg taattcagcc agaaagtaca    3360
tgtctcccat tgggaggatt tggtgttaaa taccaaactg ctagccctag tattatggag    3420
atgaacatga tgatgtaact tgtaatagca gaatagttaa tgaatgaaac tagttcttat    3480
aatttatctt tatttaaaag cttagcctgc cttaaaacta gagatcaact ttctcagctg    3540
caaaagcttc tagtctttca agaagttcat actttatgaa attgcacagt aagcatttat    3600
ttttcagacc attttgaac atcactccta aattaataaa gtattcctct gttgctttag    3660
tatttattac aataaaaagg gtttgaaata tagctgttct ttatgcataa aacacccagc    3720
taggaccatt actgccagag aaaaaaatcg tattgaatgg ccatttccct acttataaga    3780
tgtctcaatc tgaattttatt tggctacact aaagaatgca gtatatttag ttttccattt    3840
gcatgatgtt tgtgtgctat agatgatatt ttaaattgaa aagtttgttt taaattattt    3900
```

-continued

```
ttacagtgaa gactgttttc agctcttttt atattgtaca tagtctttta tgtaatttac    3960
tggcatatgt tttgtagact gtttaatgac tggatatctt ccttcaactt ttgaaataca    4020
aaaccagtgt ttttacttg tacactgttt taaagtctat taaaattgtc atttgacttt     4080
tttctgttaa cttaaaaaaa aaaaaaaaa                                      4110
```

<210> SEQ ID NO 2
<211> LENGTH: 747
<212> TYPE: PRT
<213> ORGANISM: Homo sapiens

<400> SEQUENCE: 2

```
Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335
```

-continued

```
Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Val Leu Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745
```